(12) United States Patent
Einav et al.

(10) Patent No.: US 11,699,320 B2
(45) Date of Patent: Jul. 11, 2023

(54) APPARATUSES AND METHODS FOR DEDICATED SENSORS USED IN PHARMACEUTICAL PACKAGING AND DISPENSING DEVICES

(71) Applicant: Tech Pharmacy Services, LLC, Fort Lee, NJ (US)

(72) Inventors: Omer Einav, Kfar-Monash (IL); Doron Shabanov, Tzur-Yigal (IL); Tamir Ben David, Tel-Aviv (IL); Anthony Joseph Spero, Queensbury, NY (US); Eyal Livschitz, Givat Shmuel (IL); Thomas A. Mckinney, Boonton, NJ (US); Moshe Liberman, Yehud (IL)

(73) Assignee: Tech Pharmacy Services, LLC, Fort Lee, NJ (US)

( * ) Notice: Subject to any disclaimer, the term of this patent is extended or adjusted under 35 U.S.C. 154(b) by 0 days.

(21) Appl. No.: 16/988,770

(22) Filed: Aug. 10, 2020

(65) Prior Publication Data
US 2022/0044516 A1 Feb. 10, 2022

(51) Int. Cl.
*G07F 17/00* (2006.01)
*G16H 20/13* (2018.01)
*G16H 10/60* (2018.01)
*G16H 40/63* (2018.01)

(52) U.S. Cl.
CPC ......... *G07F 17/0092* (2013.01); *G16H 10/60* (2018.01); *G16H 20/13* (2018.01); *G16H 40/63* (2018.01)

(58) Field of Classification Search
CPC .... G07F 17/0092; G16H 40/63; G16H 10/60; G16H 20/13

USPC .................................................. 700/231–244
See application file for complete search history.

(56) References Cited

U.S. PATENT DOCUMENTS

| | | | |
|---|---|---|---|
| 5,405,048 A | 4/1995 | Rogers et al. | |
| 7,228,198 B2* | 6/2007 | Vollm | G07F 11/44 700/235 |
| 7,532,948 B2* | 5/2009 | Vollm | G07F 11/44 700/244 |
| 7,753,229 B2* | 7/2010 | Hutchinson | B65B 5/103 221/9 |
| 7,789,267 B2* | 9/2010 | Hutchinson | G07F 11/62 221/9 |

(Continued)

FOREIGN PATENT DOCUMENTS

| | | |
|---|---|---|
| CN | 102158987 | 12/2015 |
| WO | WO 2018/012969 | 1/2018 |

(Continued)

OTHER PUBLICATIONS

International Search Report and the Written Opinion dated Oct. 29, 2021 From the International Searching Authority Re. Application No. PCT/IB2021/057085. (13 Pages).

(Continued)

*Primary Examiner* — Michael Collins

(57) ABSTRACT

A pharmaceutical dispensing machine comprising a plurality of modules, said plurality of modules comprise one or more sensors configured to monitor at least one pharmaceutical during a pharmaceutical dispensing process and alert when said at least one pharmaceutical is not detected by at least one of said one or more sensors.

25 Claims, 17 Drawing Sheets

(56) References Cited

U.S. PATENT DOCUMENTS

| | | | | |
|---|---|---|---|---|
| 7,831,334 | B2* | 11/2010 | Vollm | G07F 11/58 221/210 |
| 7,840,307 | B2* | 11/2010 | Mauger | G07F 11/62 700/242 |
| 8,054,086 | B2* | 11/2011 | Rivenbark, Jr. | G07F 17/0092 324/555 |
| 8,108,068 | B1* | 1/2012 | Boucher | G01G 17/00 700/240 |
| 8,393,495 | B2* | 3/2013 | Kim | B65G 27/02 221/12 |
| 8,756,998 | B1* | 6/2014 | Joplin | G01V 1/00 221/9 |
| 9,037,285 | B2* | 5/2015 | Vollm | G07F 17/0092 700/214 |
| 9,980,880 | B1 | 5/2018 | Litton | |
| 10,073,954 | B2* | 9/2018 | Chen | G16H 40/67 |
| 10,360,751 | B2* | 7/2019 | Berg | G16H 70/20 |
| 2006/0124656 | A1 | 6/2006 | Popovich, Jr. | |
| 2007/0186514 | A1* | 8/2007 | Vollm | G07F 11/54 53/247 |
| 2008/0119958 | A1* | 5/2008 | Bear | A61J 7/0481 700/244 |
| 2009/0272757 | A1* | 11/2009 | Rivenbark, Jr. | G07F 11/163 221/312 R |
| 2010/0332021 | A1* | 12/2010 | Rivenbark, Jr. | G07F 17/0092 700/231 |
| 2014/0025199 | A1* | 1/2014 | Berg | G07F 17/0092 700/232 |
| 2016/0122060 | A1 | 5/2016 | Sweet et al. | |
| 2019/0196042 | A1 | 6/2019 | Heikkila et al. | |
| 2019/0295708 | A1 | 9/2019 | Fateh | |
| 2021/0354313 | A1* | 11/2021 | Kohen | G07F 17/0092 |
| 2022/0202652 | A1* | 6/2022 | Skeuse | A61J 7/0069 |

FOREIGN PATENT DOCUMENTS

| WO | WO 2018/078618 | 5/2018 |
|---|---|---|
| WO | WO 2022/034432 | 2/2022 |

OTHER PUBLICATIONS

International Preliminary Report on Patentability Feb. 23, 2023 From the International Bureau of WIPO Re. Application No. PCT IB2021/057085. (9 Pages).

* cited by examiner

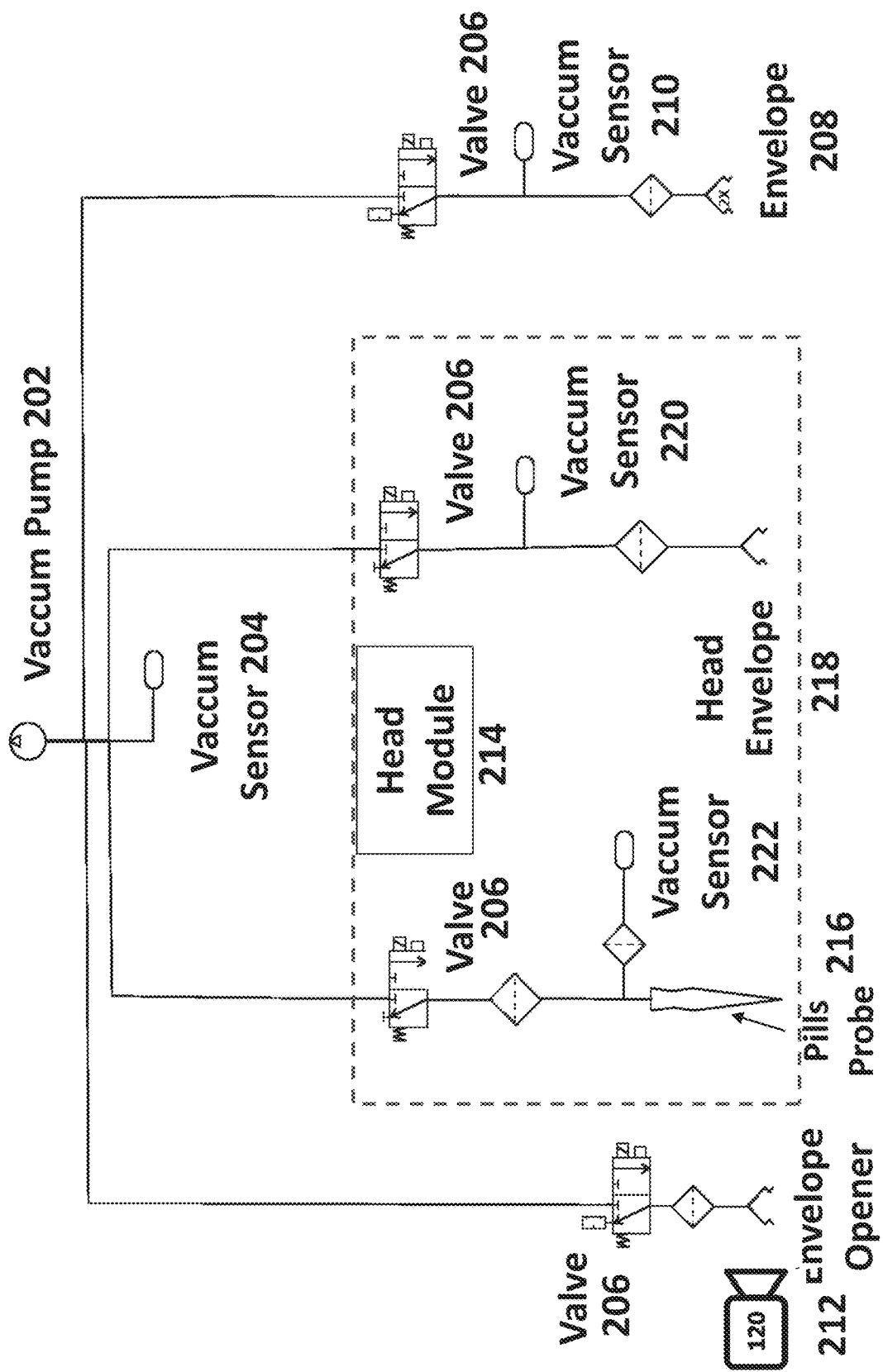

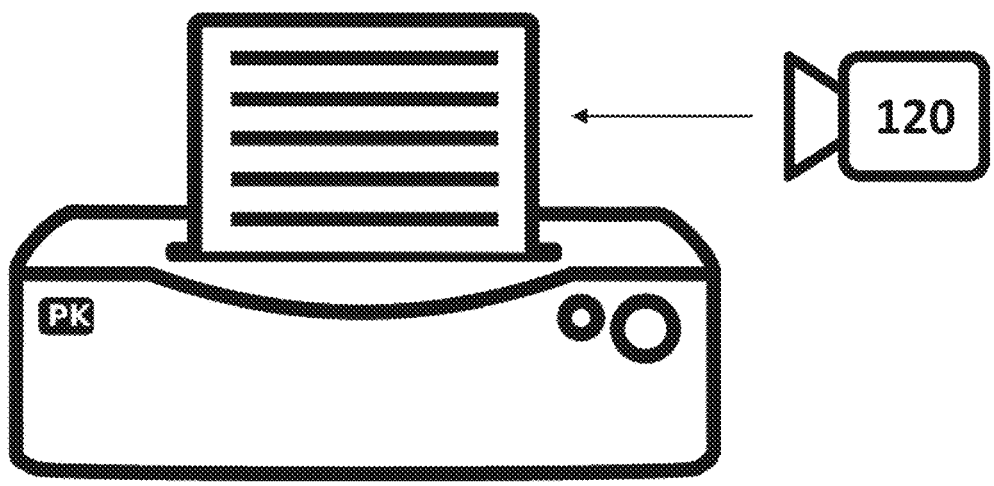
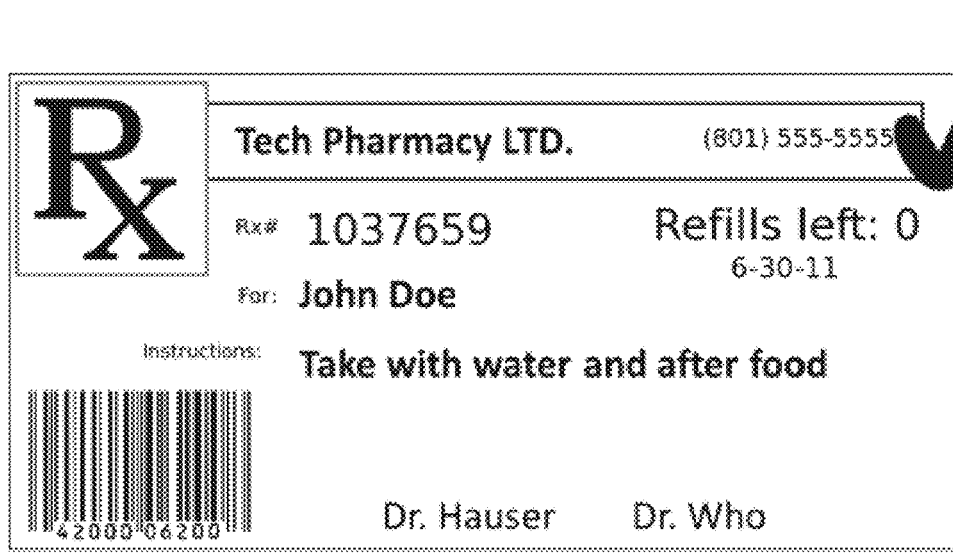
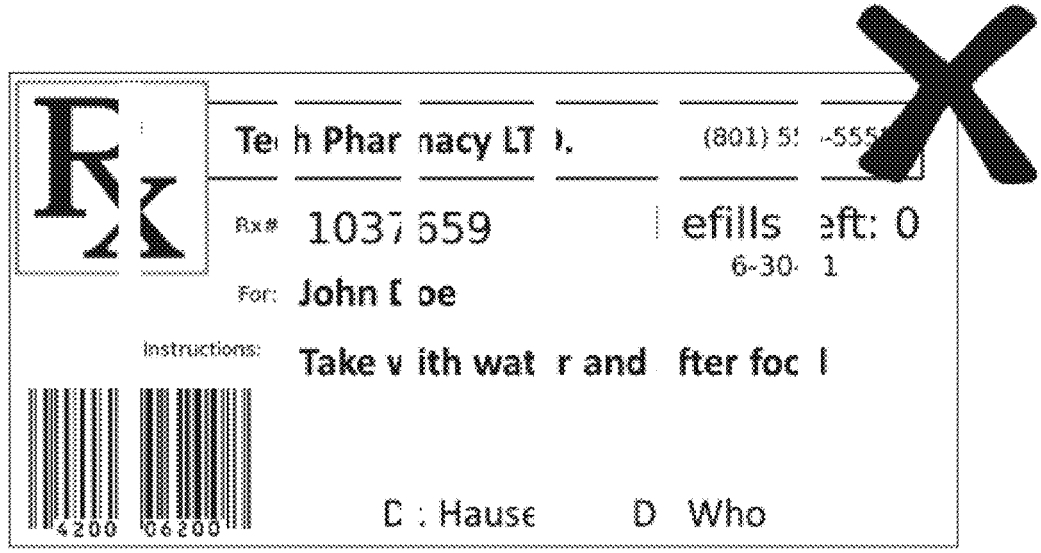
Figure 13

APPARATUSES AND METHODS FOR DEDICATED SENSORS USED IN PHARMACEUTICAL PACKAGING AND DISPENSING DEVICES

FIELD AND BACKGROUND OF THE INVENTION

The present invention, in some embodiments thereof, relates to apparatuses and methods for sensors used in packaging and dispensing machines and, more particularly, but not exclusively, to apparatuses and methods for dedicated sensors used in pharmaceutical packaging and dispensing machines.

SUMMARY OF THE INVENTION

Following is a non-exclusive list including some examples of embodiments of the invention. The invention also includes embodiments, which include fewer than all the features in an example and embodiments using features from multiple examples, also if not expressly listed below.

Example 1. A pharmaceutical dispensing machine configured to perform a pharmaceutical dispensing process including recovering at least one pharmaceutical ready-to-be-taken-by-a-patient from a general container and relaying said at least one pharmaceutical to the inside of at least one dedicated container, said pharmaceutical dispensing machine comprising a plurality of parts where said at least one pharmaceutical is passed from one to another, wherein said plurality parts comprise one or more sensors configured to alert when said at least one pharmaceutical is not detected according to expected predetermined detection values.

Example 2. The pharmaceutical dispensing machine according to example 1, further comprising a pharmaceutical identification element configured to identify said at least one pharmaceutical before said at least one pharmaceutical is passed from one part to another part.

Example 3. The pharmaceutical dispensing machine according to examples 1 or 2, wherein said one or more sensors monitor detection of said at least one pharmaceuticals before, during and/or after said pharmaceutical dispensing process.

Example 4. The pharmaceutical dispensing machine according to any one of examples 1-3, wherein the cause that said at least one pharmaceutical is not detected is that said at least one pharmaceutical fell.

Example 5. The pharmaceutical dispensing machine according to any one of examples 1-4, wherein said one or more sensors are further configured to monitor the hardware that actuates said pharmaceutical dispensing process.

Example 6. The pharmaceutical dispensing machine according to any one of examples 1-5, wherein said one or more sensors are one or more of movement sensors configured to detect movement of one or more of said plurality of parts.

Example 7. The pharmaceutical dispensing machine according to any one of examples 1-6, wherein said one or more sensors are one or more of weight sensors configured to detect said at least one pharmaceutical when in said at least one dedicated container.

Example 8. The pharmaceutical dispensing machine according to any one of examples 1-7, wherein said one or more sensors are one or more of optical sensors configured to monitor one or more of movement of said at least one pharmaceutical and status of said at least one dedicated container.

Example 9. The pharmaceutical dispensing machine according to any one of examples 1-8, wherein said one or more sensors are one or more of vibration sensors configured to monitor vibrations of one or more of said pharmaceutical dispensing machine in general, said plurality of parts and a bottom of said pharmaceutical dispensing machine.

Example 10. The pharmaceutical dispensing machine according to any one of examples 1-9, wherein said one or more sensors are one or more of sound sensors configured to monitor sounds emitted from one or more of said pharmaceutical dispensing machine in general, said plurality of parts, sounds detected at a bottom of said pharmaceutical dispensing machine and sounds detected outside said pharmaceutical dispensing machine.

Example 11. The pharmaceutical dispensing machine according to any one of examples 1-10, wherein said one or more sensors are one or more of vacuum sensors configured to monitor vacuum values of one or more of a part of said pharmaceutical dispensing machine that performs said relaying of said at least one pharmaceutical, a part of said pharmaceutical dispensing machine that performs opening of said at least one dedicated container, a part of said pharmaceutical dispensing machine that picks up said at least one dedicated container and a part of said pharmaceutical dispensing machine that provides vacuum to said one or more parts.

Example 12. The pharmaceutical dispensing machine according to any one of examples 1-11, wherein said one or more sensors are active during said recovering and said relaying.

Example 13. The pharmaceutical dispensing machine according to any one of examples 1-12, wherein said one or more sensors are active after said recovering and said relaying.

Example 14. The pharmaceutical dispensing machine according to any one of examples 1-13, wherein said pharmaceutical dispensing machine further comprises a video camera configured to visually monitor said pharmaceutical dispensing process.

Example 15. The pharmaceutical dispensing machine according to any one of examples 1-14, wherein said one or more sensors are configured to provide detection data and said pharmaceutical dispensing machine is configured to compare said detection data with a database of known detection data in order to identify said detection data.

Example 16. The pharmaceutical dispensing machine according to any one of examples 1-15, wherein said sound sensor is configured to detect the noise made due to said at least one pharmaceutical falling inside said pharmaceutical dispensing machine.

Example 17. The pharmaceutical dispensing machine according to any one of examples 1-16, wherein said vibration sensor is configured to detect the vibration made due to said at least one pharmaceutical falling inside said pharmaceutical dispensing machine.

Example 18. The pharmaceutical dispensing machine according to any one of examples 1-17, wherein said one or more sensors are configured to alert when said general containers are empty.

Example 19. The pharmaceutical dispensing machine according to any one of examples 1-18, wherein said one or more sensors are configured to alert when said dedicated containers are not open.

Example 20. The pharmaceutical dispensing machine according to any one of examples 1-19, wherein said one or more sensors are configured to alert when said dedicated containers are not detected.

Example 21. The pharmaceutical dispensing machine according to any one of examples 1-20, wherein said one or more sensors are configured to alert when said dedicated containers are empty.

Example 22. The pharmaceutical dispensing machine according to any one of examples 1-21, wherein said one or more sensors are configured to alert when said dedicated containers contain a different number of pills than expected.

Example 23. The pharmaceutical dispensing machine according to any one of examples 1-22, wherein said one or more sensors are configured to alert when said dedicated containers contain a different type of pharmaceutical than expected.

Example 24. The pharmaceutical dispensing machine according to any one of examples 1-23, wherein said one or more sensors are add-on hardware to an existing pharmaceutical dispensing machine.

Example 25. The pharmaceutical dispensing machine according to any one of examples 1-24, wherein said one or more sensors are built-in sensors in said plurality of parts.

Example 26. The pharmaceutical dispensing machine according to any one of examples 1-25, wherein when a problem is detected with a specific dedicated container from said one or more dedicated containers, said specific dedicated container is discarded and said pharmaceutical dispensing process is reinitiated.

Example 27. The pharmaceutical dispensing machine according to any one of examples 1-26, further comprising a waste bin for receiving discarded dedicated containers.

Example 28. The pharmaceutical dispensing machine according to any one of examples 1-27, wherein when said pharmaceutical dispensing machine detect problems from two consecutive of said dedicated containers from a same bulk of dedicated containers, said pharmaceutical dispensing machine changes bulk of dedicated containers.

Example 29. The pharmaceutical dispensing machine according to any one of examples 1-28, wherein said at least one dedicated container is at least one envelope.

Example 30. The pharmaceutical dispensing machine according to any one of examples 1-29, wherein said relaying comprises relaying a single pharmaceutical each time.

Example 31. A pharmaceutical dispensing machine configured to perform a pharmaceutical dispensing process including recovering at least one pharmaceutical ready-to-be-taken-by-a-patient from a general container and relaying said at least one pharmaceutical to the inside of at least one dedicated container, said pharmaceutical dispensing machine comprising a plurality of parts where said at least one pharmaceutical is passed from one to another, wherein said plurality parts comprise one or more sensors configured to alert when said at least one dedicated container is detected not according to an expected determined state.

Example 32. The pharmaceutical dispensing machine according to example 31, wherein said determined state is one or more of open, close and right orientation.

Example 33. The pharmaceutical dispensing machine according to examples 31 or 32, wherein said one or more sensors monitor detection of said at least one dedicated container before, during and/or after said pharmaceutical dispensing process.

Example 34. The pharmaceutical dispensing machine according to any one of examples 31-33, wherein the cause that said at least one dedicated container is detected not according to an expected determined state is that said at least one dedicated container is one or more of not open, partially open, not close, partially close, not in the right orientation.

Example 35. The pharmaceutical dispensing machine according to any one of examples 31-34, wherein said at least one dedicated container is at least one envelope.

Example 36. The pharmaceutical dispensing machine according to any one of examples 31-35, wherein said one or more sensors are further configured to monitor the hardware that actuates said pharmaceutical dispensing process.

Example 37. The pharmaceutical dispensing machine according to any one of examples 31-36, wherein said one or more sensors are one or more of movement sensors configured to detect movement of one or more of said plurality of parts.

Example 38. The pharmaceutical dispensing machine according to any one of examples 31-37, wherein said one or more sensors are one or more of weight sensors configured to detect said at least one pharmaceutical when in said at least one dedicated container.

Example 39. The pharmaceutical dispensing machine according to any one of examples 31-38, wherein said one or more sensors are one or more of optical sensors configured to monitor one or more of movement of said at least one pharmaceutical, status of said at least one dedicated container.

Example 40. The pharmaceutical dispensing machine according to any one of examples 31-39, wherein said one or more sensors are one or more of vibration sensors configured to monitor vibrations of one or more of said pharmaceutical dispensing machine in general, said plurality of parts, a bottom of said pharmaceutical dispensing machine.

Example 41. The pharmaceutical dispensing machine according to any one of examples 31-40, wherein said one or more sensors are one or more of sound sensors configured to monitor sounds emitted from one or more of said pharmaceutical dispensing machine in general, said plurality of parts, sounds detected at a bottom of said pharmaceutical dispensing machine, sounds detected outside said pharmaceutical dispensing machine.

Example 42. The pharmaceutical dispensing machine according to any one of examples 31-41, wherein said one or more sensors are one or more of vacuum sensors configured to monitor vacuum values of one or more of a part of said pharmaceutical dispensing machine that performs said relaying of said at least one pharmaceutical, a part of said pharmaceutical dispensing machine that performs opening of said at least one dedicated container, a part of said pharmaceutical dispensing machine that picks up said at least one dedicated container, a part of said pharmaceutical dispensing machine that provides vacuum to said one or more parts.

Example 43. The pharmaceutical dispensing machine according to any one of examples 31-42, wherein said one or more sensors are configured to provide detection data and said pharmaceutical dispensing machine is configured to compare said detection data with a database of known detection data in order to identify said detection data.

Example 44. The pharmaceutical dispensing machine according to any one of examples 31-43, wherein said vibration sensor is configured to detect the vibration made due to said at least one pharmaceutical falling inside said pharmaceutical dispensing machine.

Example 45. The pharmaceutical dispensing machine according to any one of examples 31-44, wherein said one or more sensors are configured to alert when said dedicated containers are empty.

Example 46. The pharmaceutical dispensing machine according to any one of examples 31-45, wherein said one or more sensors are configured to alert when said dedicated containers contain a different number of pills than expected.

Example 47. The pharmaceutical dispensing machine according to any one of examples 31-46, wherein said one or more sensors are configured to alert when said dedicated containers contain a different type of pills than expected.

Example 48. The pharmaceutical dispensing machine according to any one of examples 31-47, wherein said one or more sensors are active during said recovering and said relaying.

Example 49. The pharmaceutical dispensing machine according to any one of examples 31-48, wherein said one or more sensors are active after said recovering and said relaying.

Example 50. The pharmaceutical dispensing machine according to any one of examples 31-49, wherein said pharmaceutical dispensing machine further comprises a video camera configured to visually monitor said pharmaceutical dispensing process.

Example 51. The pharmaceutical dispensing machine according to any one of examples 31-50, wherein said pharmaceutical dispensing machine further comprises a sound sensor configured to monitor noises inside said pharmaceutical dispensing machine.

Example 52. The pharmaceutical dispensing machine according to any one of examples 31-51, wherein said sound sensor is configured to detect a noise and said pharmaceutical dispensing machine is configured to compare said noise with a database of noises in order to identify said noise.

Example 53. The pharmaceutical dispensing machine according to any one of examples 31-52, wherein said sound sensor is configured to detect the noise made due to said at least one pharmaceutical falling inside said pharmaceutical dispensing machine.

Example 54. The pharmaceutical dispensing machine according to any one of examples 31-53, wherein said one or more sensors are configured to alert when said general containers are empty.

Example 55. The pharmaceutical dispensing machine according to any one of examples 31-54, wherein said one or more sensors are configured to alert when said dedicated containers are not detected.

Example 56. The pharmaceutical dispensing machine according to any one of examples 31-55, wherein said one or more sensors are add-on hardware to an existing pharmaceutical dispensing machine.

Example 57. The pharmaceutical dispensing machine according to any one of examples 31-56, wherein said one or more sensors are built-in sensors in said plurality of modules.

Example 58. The pharmaceutical dispensing machine according to any one of examples 31-57, further comprising a pharmaceutical identification element configured to identify said at least one pharmaceutical before said at least one pharmaceutical is passed from one part to another part.

Example 59. The pharmaceutical dispensing machine according to any one of examples 31-58, wherein when a problem is detected with a specific dedicated container from said one or more dedicated containers, said specific dedicated container is discarded and said pharmaceutical dispensing process is reinitiated.

Example 60. The pharmaceutical dispensing machine according to any one of examples 31-59, further comprising a waste bin for receiving discarded dedicated containers.

Example 61. The pharmaceutical dispensing machine according to any one of examples 31-60, wherein when said pharmaceutical dispensing machine detect problems from at least two consecutive of said dedicated containers from a same bulk of dedicated containers, said pharmaceutical dispensing machine changes bulk of dedicated containers.

Example 62. The pharmaceutical dispensing machine according to any one of examples 31-61, wherein said relaying comprises relaying a single pharmaceutical each time.

Example 63. A pharmaceutical dispensing machine configured to perform a pharmaceutical dispensing process including recovering at least one pharmaceutical ready-to-be-taken-by-a-patient from a general container and relaying said at least one pharmaceutical to the inside of at least one dedicated container, said pharmaceutical dispensing machine comprising a plurality of parts where said at least one pharmaceutical is passed from one to another, wherein said pharmaceutical dispensing machine comprise one or more sensors configured to alert when said at least one pharmaceutical is detected in a place other than on said plurality of parts.

Example 64. The pharmaceutical dispensing machine according to example 63, wherein said one or more sensors monitor detection of said at least one pharmaceuticals before, during and/or after said pharmaceutical dispensing process.

Example 65. The pharmaceutical dispensing machine according to examples 63 or 64, wherein the cause that said at least one pharmaceutical is detected in a place other than on said plurality of parts is that said at least one pharmaceutical fell.

Example 66. The pharmaceutical dispensing machine according to any one of examples 63-65, wherein said one or more sensors are further configured to monitor the hardware that actuates said pharmaceutical dispensing process.

Example 67. The pharmaceutical dispensing machine according to any one of examples 63-66, wherein said one or more sensors are one or more of movement sensors configured to detect movement of one or more of said plurality of parts.

Example 68. The pharmaceutical dispensing machine according to any one of examples 63-67, wherein said one or more sensors are one or more of weight sensors configured to detect said at least one pharmaceutical when in said at least one dedicated container.

Example 69. The pharmaceutical dispensing machine according to any one of examples 63-68, wherein said one or more sensors are one or more of optical sensors configured to monitor one or more of movement of said at least one pharmaceutical, status of said at least one dedicated container.

Example 70. The pharmaceutical dispensing machine according to any one of examples 63-69, wherein said one or more sensors are one or more of vibration sensors configured to monitor vibrations of one or more of said pharmaceutical dispensing machine in general, said plurality of parts, a bottom of said pharmaceutical dispensing machine.

Example 71. The pharmaceutical dispensing machine according to any one of examples 63-70, wherein said one or more sensors are one or more of sound sensors configured to monitor sounds emitted from one or more of said pharmaceutical dispensing machine in general, said plurality of parts, sounds detected at a bottom of said pharmaceutical dispensing machine, sounds detected outside said pharmaceutical dispensing machine.

Example 72. The pharmaceutical dispensing machine according to any one of examples 63-71, wherein said one or more sensors are one or more of vacuum sensors configured to monitor vacuum values of one or more of a part of said pharmaceutical dispensing machine that performs said relaying of said at least one pharmaceutical, a part of said pharmaceutical dispensing machine that performs opening of said at least one dedicated container, a part of said pharmaceutical dispensing machine that picks up said at least one dedicated container, a part of said pharmaceutical dispensing machine that provides vacuum to said one or more parts.

Example 73. The pharmaceutical dispensing machine according to any one of examples 63-72, wherein said one or more sensors are active during said recovering and said relaying.

Example 74. The pharmaceutical dispensing machine according to any one of examples 63-73, wherein said one or more sensors are active after said recovering and said relaying.

Example 75. The pharmaceutical dispensing machine according to any one of examples 63-74, wherein said pharmaceutical dispensing machine further comprises a video camera configured to visually monitor said pharmaceutical dispensing process.

Example 76. The pharmaceutical dispensing machine according to any one of examples 63-75, wherein said one or more sensors are configured to provide detection data and said pharmaceutical dispensing machine is configured to compare said detection data with a database of known detection data in order to identify said detection data.

Example 77. The pharmaceutical dispensing machine according to any one of examples 63-76, wherein said sound sensor is configured to detect a noise and said pharmaceutical dispensing machine is configured to compare said noise with a database of noises in order to identify said noise.

Example 78. The pharmaceutical dispensing machine according to any one of examples 63-77, wherein said vibration sensor is configured to detect the vibration made due to said at least one pharmaceutical falling inside said pharmaceutical dispensing machine.

Example 79. The pharmaceutical dispensing machine according to any one of examples 63-78, wherein said sound sensor is configured to detect the noise made due to said at least one pharmaceutical falling inside said pharmaceutical dispensing machine.

Example 80. The pharmaceutical dispensing machine according to any one of examples 63-79, wherein said one or more sensors are configured to alert when said general containers are empty.

Example 81. The pharmaceutical dispensing machine according to any one of examples 63-80, wherein said one or more sensors are configured to alert when said dedicated containers are not open.

Example 82. The pharmaceutical dispensing machine according to any one of examples 63-81, wherein said one or more sensors are configured to alert when said dedicated containers are not detected.

Example 83. The pharmaceutical dispensing machine according to any one of examples 63-82, wherein said one or more sensors are configured to alert when said dedicated containers are empty.

Example 84. The pharmaceutical dispensing machine according to any one of examples 63-83, wherein said one or more sensors are configured to alert when said dedicated containers contain a different number of pills than expected.

Example 85. The pharmaceutical dispensing machine according to any one of examples 63-84, wherein said one or more sensors are configured to alert when said dedicated containers contain a different type of pills than expected.

Example 86. The pharmaceutical dispensing machine according to any one of examples 63-85, wherein said one or more sensors are add-on hardware to an existing pharmaceutical dispensing machine.

Example 87. The pharmaceutical dispensing machine according to any one of examples 63-86, wherein said one or more sensors are built-in sensors in said plurality of parts.

Example 88. The pharmaceutical dispensing machine according to any one of examples 63-87, wherein when a problem is detected with a specific dedicated container from said one or more dedicated containers, said specific dedicated container is discarded and said pharmaceutical dispensing process is reinitiated.

Example 89. The pharmaceutical dispensing machine according to any one of examples 63-88, further comprising a waste bin for receiving discarded dedicated containers.

Example 90. The pharmaceutical dispensing machine according to any one of examples 63-89, wherein when said pharmaceutical dispensing machine detect problems from two of said dedicated containers from a same bulk of dedicated containers, said pharmaceutical dispensing machine changes bulk of dedicated containers.

Example 91. The pharmaceutical dispensing machine according to any one of examples 63-90, wherein said at least one dedicated container is at least one envelope.

Example 92. The pharmaceutical dispensing machine according to any one of examples 63-91, wherein said relaying comprises relaying a single pharmaceutical each time.

Example 93. A method of monitoring the successful relaying at least one pharmaceutical by a vacuum-based relaying part in a pharmaceutical dispensing machine, said pharmaceutical dispensing machine further comprising a plurality of parts where said at least one pharmaceutical is relayed from one to another by said vacuum-based relaying part and at least one processor comprising instructions for monitoring pressure values, the method comprising:
   a. providing at least one vacuum sensor to said vacuum-based relaying part configured to detect pressure vacuum values;
   b. comparing said detected pressure values with expected pressure values and generating an output signal informing of a result of said comparing.

Example 94. The method according to example 93, wherein said at least one vacuum sensor monitor vacuum values before, during and/or after said relaying of said at least one pharmaceutical.

Example 95. The method according to examples 93 or 94, wherein the cause that said detected pressure values are different from said expected pressure values is that said at least one pharmaceutical fell.

Example 96. The method according to any one of examples 93-95, wherein said pharmaceutical dispensing machine further comprises one or more sensors that are further configured to monitor the hardware that actuates a pharmaceutical dispensing process.

Example 97. The method according to any one of examples 93-96, wherein said one or more sensors are one or more of movement sensors configured to detect movement of one or more of said plurality of parts.

Example 98. The method according to any one of examples 93-97, wherein said one or more sensors are one or more of weight sensors configured to detect said at least one pharmaceutical when in said at least one dedicated container.

Example 99. The method according to any one of examples 93-98, wherein said one or more sensors are one or more of optical sensors configured to monitor one or more of movement of said at least one pharmaceutical, status of said at least one dedicated container.

Example 100. The method according to any one of examples 93-99, wherein said one or more sensors are one or more of vibration sensors configured to monitor vibrations of one or more of said pharmaceutical dispensing machine in general, said plurality of parts, a bottom of said pharmaceutical dispensing machine.

Example 101. The method according to any one of examples 93-100, wherein said one or more sensors are one or more of sound sensors configured to monitor sounds emitted from one or more of said pharmaceutical dispensing machine in general, said plurality of parts, sounds detected at a bottom of said pharmaceutical dispensing machine, sounds detected outside said pharmaceutical dispensing machine.

Example 102. The method according to any one of examples 93-101, wherein said one or more sensors are one or more of vacuum sensors configured to monitor vacuum values of one or more of a part of said pharmaceutical dispensing machine that performs said relaying of said at least one pharmaceutical, a part of said pharmaceutical dispensing machine that performs opening of said at least one dedicated container, a part of said pharmaceutical dispensing machine that picks up said at least one dedicated container, a part of said pharmaceutical dispensing machine that provides vacuum to said one or more parts.

Example 103. The method according to any one of examples 93-102, wherein said one or more sensors are active during said recovering and said relaying.

Example 104. The method according to any one of examples 93-103, wherein said one or more sensors are active after said recovering and said relaying.

Example 105. The method according to any one of examples 93-104, wherein said pharmaceutical dispensing machine further comprises a video camera configured to visually monitor said pharmaceutical dispensing process.

Example 106. The method according to any one of examples 93-105, wherein said one or more sensors are configured to provide detection data and said pharmaceutical dispensing machine is configured to compare said detection data with a database of known detection data in order to identify said detection data.

Example 107. The method according to any one of examples 93-106, wherein said sound sensor is configured to detect a noise and said pharmaceutical dispensing machine is configured to compare said noise with a database of noises in order to identify said noise.

Example 108. The method according to any one of examples 93-107, wherein said sound sensor is configured to detect the noise made due to said at least one pharmaceutical falling inside said pharmaceutical dispensing machine.

Example 109. The method according to any one of examples 93-108, wherein said vibration sensor is configured to detect the vibration made due to said at least one pharmaceutical falling inside said pharmaceutical dispensing machine.

Example 110. The method according to any one of examples 93-109, wherein said one or more sensors are add-on hardware to an existing pharmaceutical dispensing machine.

Example 111. The method according to any one of examples 93-110, wherein said one or more sensors are built-in sensors in said plurality of parts.

Example 112. The method according to any one of examples 93-111, wherein said one or more sensors are configured to alert when said dedicated containers are empty.

Example 113. The method according to any one of examples 93-112, wherein said one or more sensors are configured to alert when said dedicated containers contain a different number of pills than expected.

Example 114. The method according to any one of examples 93-113, wherein said one or more sensors are configured to alert when said dedicated containers contain a different type of pills than expected.

Example 115. The method according to any one of examples 93-114, wherein when a problem is detected with a specific dedicated container from said one or more dedicated containers, said specific dedicated container is discarded and said pharmaceutical dispensing process is reinitiated.

Example 116. The method according to any one of examples 93-115, further comprising a waste bin for receiving discarded dedicated containers.

Example 117. The method according to any one of examples 93-116, wherein when said pharmaceutical dispensing machine detect problems from two of said dedicated containers from a same bulk of dedicated containers, said pharmaceutical dispensing machine changes bulk of dedicated containers.

Example 118. The method according to any one of examples 93-117, wherein said at least one dedicated container is at least one envelope.

Example 119. The method according to any one of examples 93-118, wherein said relaying comprises relaying a single pharmaceutical each time.

Example 120. A method of relaying at least one pharmaceutical in a pharmaceutical dispensing machine, said pharmaceutical dispensing machine comprising a plurality of parts where said at least one pharmaceutical is relayed from one to another, the method comprising:
 a. providing at least one predetermined pressure profile comprising a plurality of predetermined sequential pressure values to be actuated by said at least one vacuum-based relaying part;
 b. performing said at least one predetermined pressure profile comprising said plurality of predetermined sequential pressure values when relaying said at least one pharmaceutical;
 c. comparing said performed at least one predetermined pressure profile with said at least one predetermined pressure profile;
 d. generating an output signal informing of a result of said comparing.

Example 121. The method according to example 120, wherein said performing said at least one predetermined pressure profile further comprises monitoring pressure detection values by at least one vacuum sensor.

Example 122. The method according to examples 120 or 121, wherein said at least one vacuum sensor monitor vacuum values before, during and/or after said relaying of said at least one pharmaceutical.

Example 123. The method according to any one of examples 120-122, wherein each pharmaceutical comprise a unique pressure detection value.

Example 124. The method according to any one of examples 120-123, wherein when a new pharmaceutical is inserted in said pharmaceutical dispensing machine, the method further comprises:
 a. measuring a pressure detection value of said new pharmaceutical;
 b. adding said measured pressure detection value of said new pharmaceutical to a database containing pressure profiles of pharmaceuticals.

Example 125. The method according to any one of examples 120-124, wherein the cause that said detected pressure values are different from said expected pressure values is that said at least one pharmaceutical fell.

Example 126. The method according to any one of examples 120-125, wherein said pharmaceutical dispensing machine further comprises one or more sensors that are further configured to monitor the hardware that actuates a pharmaceutical dispensing process.

Example 127. The method according to any one of examples 120-126, wherein said one or more sensors are one or more of movement sensor, weight sensor, infrared sensor, vibration sensor, sound sensor.

Example 128. The method according to any one of examples 120-127, wherein said one or more sensors are active during said recovering and said relaying.

Example 129. The method according to any one of examples 120-128 wherein said one or more sensors are active after said recovering and said relaying.

Example 130. The method according to any one of examples 120-129, wherein said pharmaceutical dispensing machine further comprises a video camera configured to visually monitor said pharmaceutical dispensing process.

Example 131. The method according to any one of examples 120-130, wherein said pharmaceutical dispensing machine further comprises a sound sensor configured to monitor noises inside said pharmaceutical dispensing machine.

Example 132. The method according to any one of examples 120-131, wherein said sound sensor is configured to detect a noise and said pharmaceutical dispensing machine is configured to compare said noise with a database of noises in order to identify said noise.

Example 133. The method according to any one of examples 120-132, wherein said sound sensor is configured to detect the noise made due to said at least one pharmaceutical falling inside said pharmaceutical dispensing machine.

Example 134. The method according to any one of examples 120-133, wherein said one or more sensors are add-on hardware to an existing pharmaceutical dispensing machine.

Example 135. The method according to any one of examples 120-134, wherein said one or more sensors are built-in sensors in said plurality of parts.

Example 136. The method according to any one of examples 120-135, wherein said at least one dedicated container is at least one envelope.

Example 137. The method according to any one of examples 120-136, wherein said relaying comprises relaying a single pharmaceutical each time.

Example 138. A method of monitoring a pharmaceutical dispensing process, said pharmaceutical dispensing process performed in a closed housing of a pharmaceutical dispensing machine, the method comprising:
 a. identifying a pharmaceutical located in a general container;
 b. monitoring correct movement of said pharmaceutical from said general container into a dedicated container;
 c. monitoring correct presence of said pharmaceutical in said dedicated container;
 d. monitoring correct movement of said dedicated container containing said pharmaceutical until it arrives at a dispensing waiting location.

Example 139. The method according to example 138, wherein said identifying said pharmaceutical located in said general container is by comparing an identification label on said general container with an identification data on a database.

Example 140. The method according to example 138 or example 139, wherein said monitoring correct movement of said pharmaceutical from said general container into said dedicated container is by comparing a detected movement data of said pharmaceutical from at least one sensor with an expected moving data on a database.

Example 141. The method according to any one of examples 138-140, wherein said monitoring correct presence of said pharmaceutical in said dedicated container is by comparing a detected presence data of said pharmaceutical from at least one sensor with an expected presence data on a database.

Example 142. The method according to any one of examples 138-141, wherein said monitoring correct movement of said dedicated container is by comparing a detected movement data of said dedicated container from at least one sensor with an expected movement data on a database.

Example 143. A pharmaceutical dispensing machine configured to perform a pharmaceutical dispensing process including recovering at least one pharmaceutical ready-to-be-taken-by-a-patient from a general container and relaying said at least one pharmaceutical to the inside of at least one dedicated container, said pharmaceutical dispensing machine comprising:
 a plurality of parts where said at least one pharmaceutical is passed from one of said plurality of parts to another of said plurality of parts to perform said recovering and said relaying;
 a controller comprising a memory storing indication of information regarding said pharmaceutical dispensing process including the order in which said at least one pharmaceutical is recovered and relayed from said general container to said at least one dedicated container;
 a plurality of sensors;
 wherein said controller utilizes one or more sensors to detect a deviation from expected predetermined detection values related to said recovering and said relaying of said at least one pharmaceutical.

Example 144. The pharmaceutical dispensing machine according to example 143, further comprising a pharmaceutical identification element configured to identify said at least one pharmaceutical before said at least one pharmaceutical is passed from one part to another part.

Example 145. The pharmaceutical dispensing machine according to example 143, wherein the cause that said at least one pharmaceutical is not detected according to expected predetermined detection values is that said at least one pharmaceutical fell.

Example 146. The pharmaceutical dispensing machine according to example 143, wherein said one or more sensors are further configured to monitor the hardware that actuates said pharmaceutical dispensing process.

Example 147. The pharmaceutical dispensing machine according to example 143, wherein said one or more sensors are one or more of weight sensors configured to detect said at least one pharmaceutical when in said at least one dedicated container.

Example 148. The pharmaceutical dispensing machine according to example 143, wherein said one or more sensors are one or more of optical sensors configured to monitor one or more of movement of said at least one pharmaceutical and status of said at least one dedicated container.

Example 149. The pharmaceutical dispensing machine according to example 143, wherein said one or more sensors are one or more of vibration sensors configured to monitor vibrations of one or more of said pharmaceutical dispensing machine in general, said plurality of parts and a bottom of said pharmaceutical dispensing machine.

Example 150. The pharmaceutical dispensing machine according to example 143, wherein said one or more sensors are one or more of sound sensors configured to monitor sounds emitted from one or more of said pharmaceutical dispensing machine in general, said plurality of parts, sounds detected at a bottom of said pharmaceutical dispensing machine and sounds detected outside said pharmaceutical dispensing machine.

Example 151. The pharmaceutical dispensing machine according to example 143, wherein said one or more sensors are one or more of vacuum sensors configured to monitor vacuum values of one or more of a part of said pharmaceutical dispensing machine that performs said relaying of said at least one pharmaceutical, a part of said pharmaceutical dispensing machine that performs opening of said at least one dedicated container, a part of said pharmaceutical dispensing machine that picks up said at least one dedicated container and a part of said pharmaceutical dispensing machine that provides vacuum to said one or more parts.

Example 152. The pharmaceutical dispensing machine according to example 143, wherein said pharmaceutical dispensing machine further comprises a video camera configured to visually monitor said pharmaceutical dispensing process.

Example 153. The pharmaceutical dispensing machine according to example 143, wherein said one or more sensors are configured to provide detection data and said pharmaceutical dispensing machine is configured to compare said detection data with a database of known detection data in order to identify said detection data.

Example 154. The pharmaceutical dispensing machine according to example 153, wherein said one or more sound sensors are configured to detect the noise made due to said at least one pharmaceutical falling inside said pharmaceutical dispensing machine.

Example 155. The pharmaceutical dispensing machine according to example 152, wherein said one or more vibration sensors are configured to detect the vibration made due to said at least one pharmaceutical falling inside said pharmaceutical dispensing machine.

Example 156. The pharmaceutical dispensing machine according to example 143, wherein said one or more sensors are configured to alert when said dedicated containers contain a different number of pills than expected.

Example 157. The pharmaceutical dispensing machine according to example 143, wherein said one or more sensors are configured to alert when said dedicated containers contain a different type of pharmaceutical than expected.

Example 158. A method of monitoring a pharmaceutical dispensing process, said pharmaceutical dispensing process performed in a closed housing of a pharmaceutical dispensing machine, the method comprising:
 a. identifying a pharmaceutical located in a general container;
 b. monitoring correct movement of said pharmaceutical from said general container into a dedicated container;
 c. monitoring correct presence of said pharmaceutical in said dedicated container;
 d. monitoring correct movement of said dedicated container containing said pharmaceutical until it arrives at a dispensing waiting location.

Example 159. The method according to example 158, wherein said monitoring correct movement of said pharmaceutical from said general container into a dedicated container further comprises monitoring one or more intermediate movements of said movements of said pharmaceutical from said general container into a dedicated container.

Example 160. The method according to example 158, wherein said identifying said pharmaceutical located in said general container is by comparing an identification label on said general container with an identification data on a database.

Example 161. The method according to example 158, wherein said monitoring correct movement of said pharmaceutical from said general container into said dedicated container is by comparing a detected movement data of said pharmaceutical from at least one sensor with an expected moving data on a database.

Example 162. The method according to example 158, wherein said monitoring correct presence of said pharmaceutical in said dedicated container is by comparing a detected presence data of said pharmaceutical from at least one sensor with an expected presence data on a database.

Example 163. The method according to example 158, wherein said monitoring correct movement of said dedicated container is by comparing a detected movement data of said dedicated container from at least one sensor with an expected movement data on a database.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as evaluating the readings from sensors, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figures 4A, 4B:
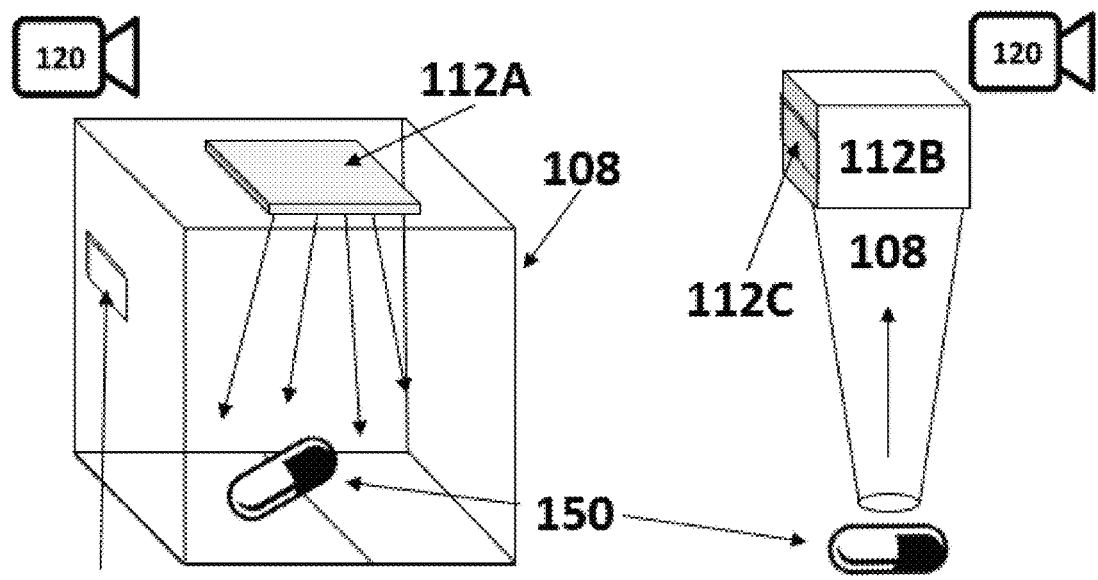
Figure 5:
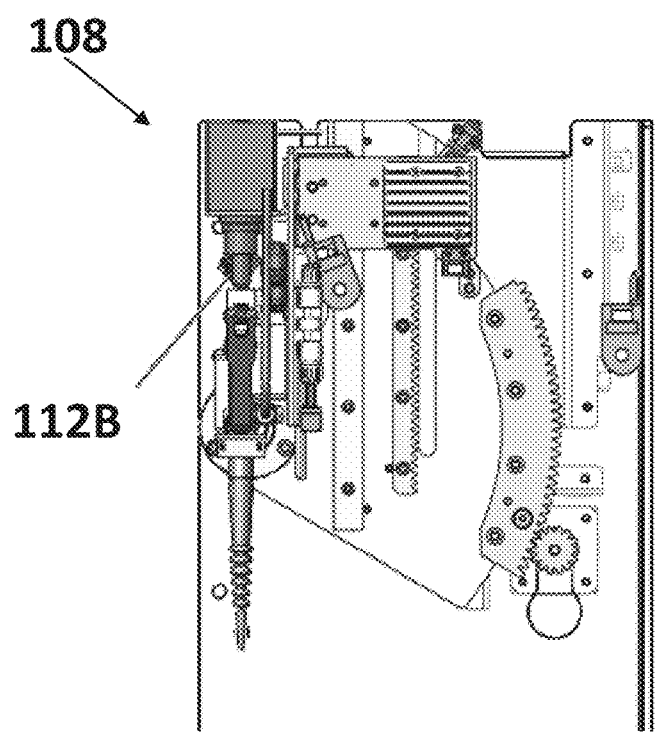
Figure 6:
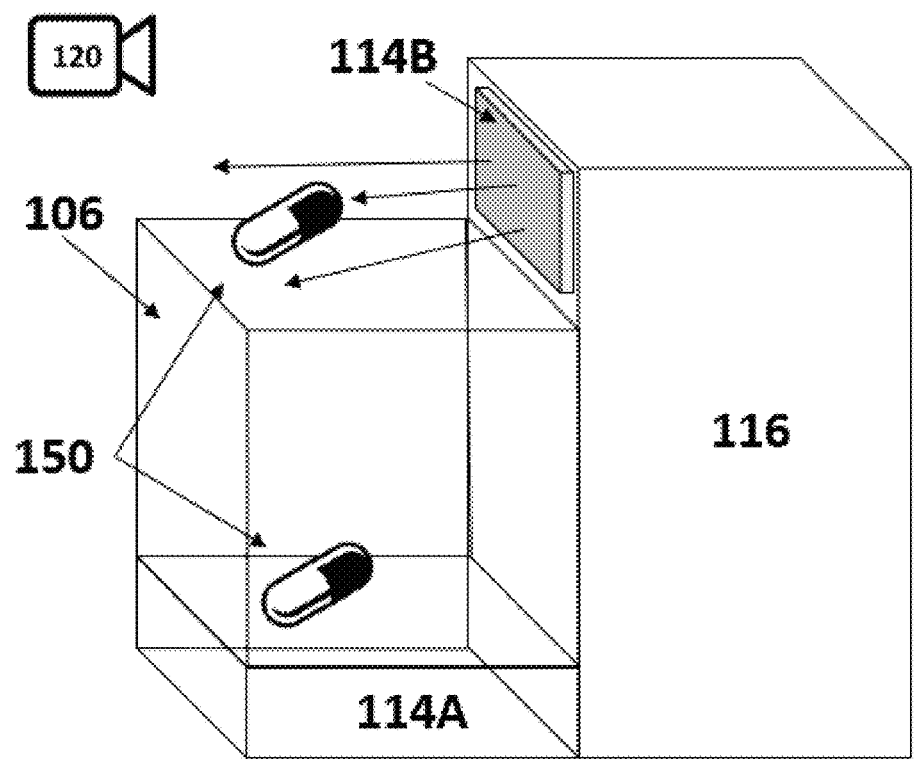
Figure 7A:
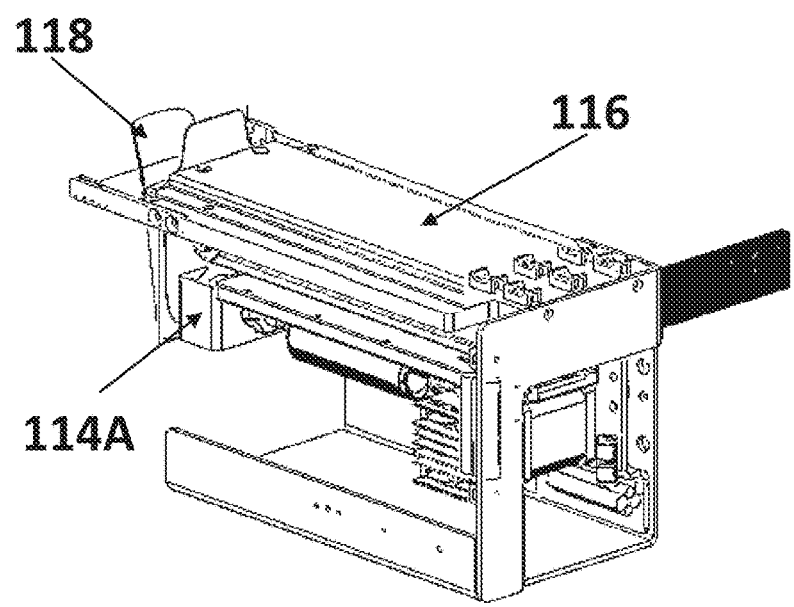
Figure 7B:
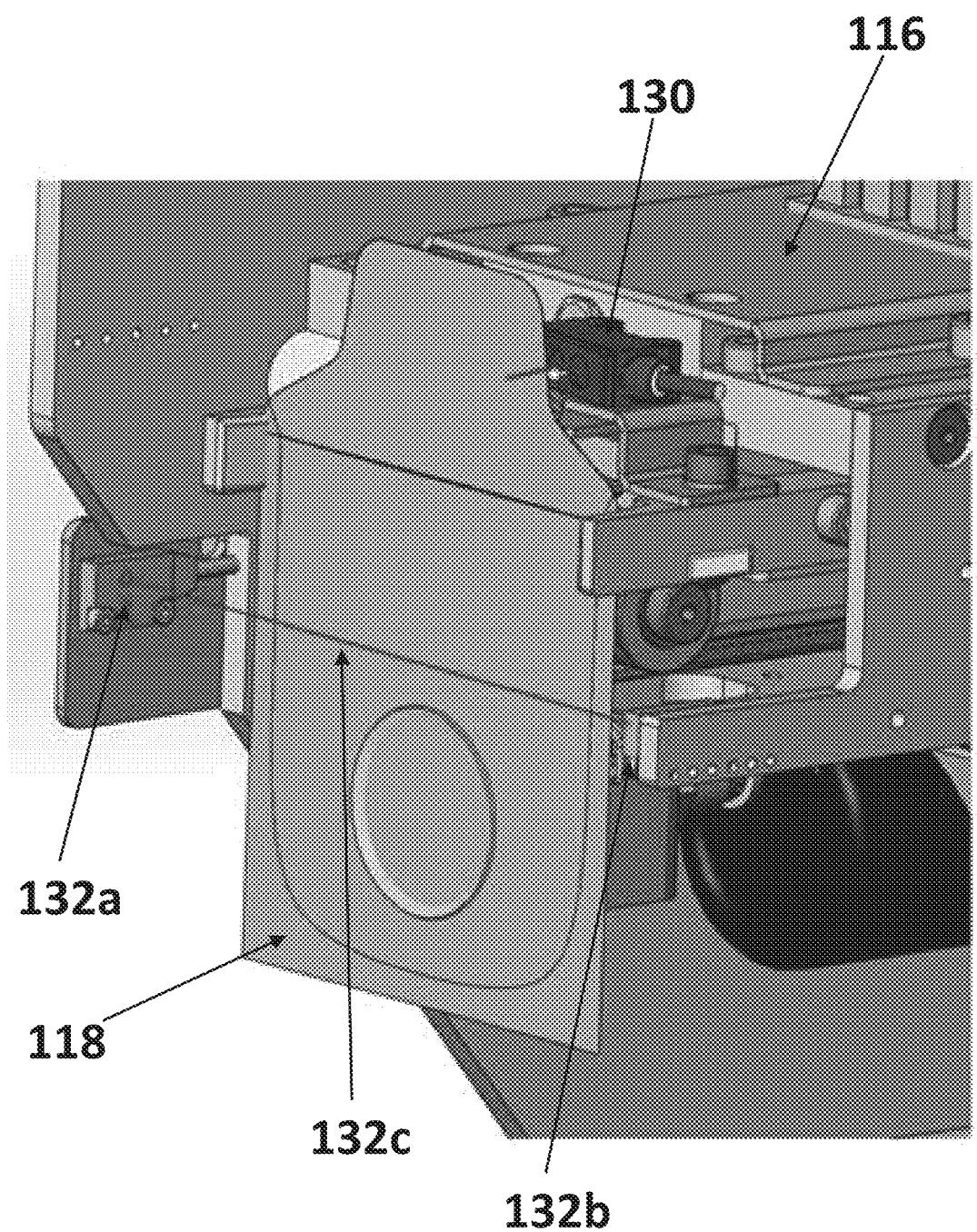
Figure 9:
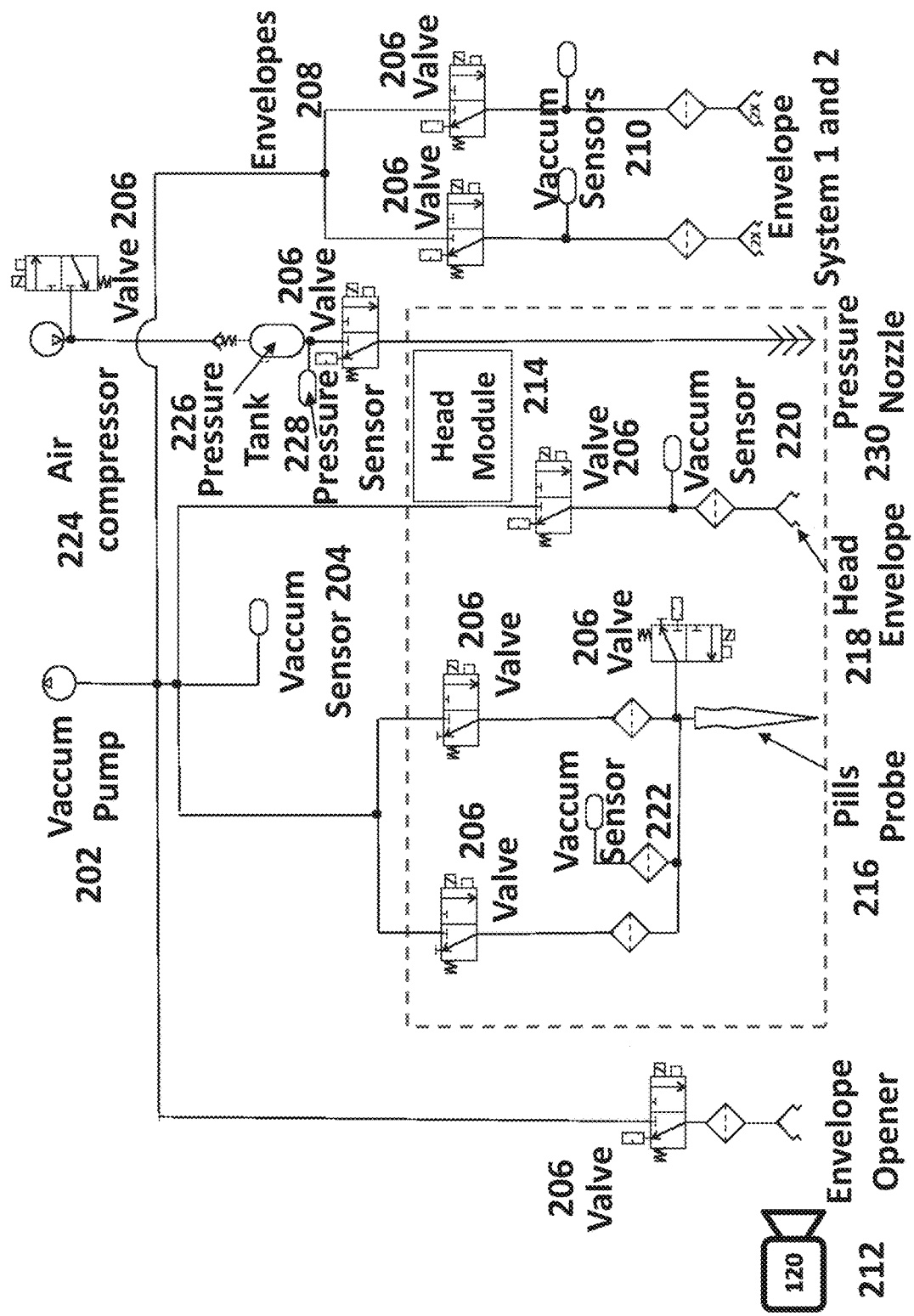
Figure 10:
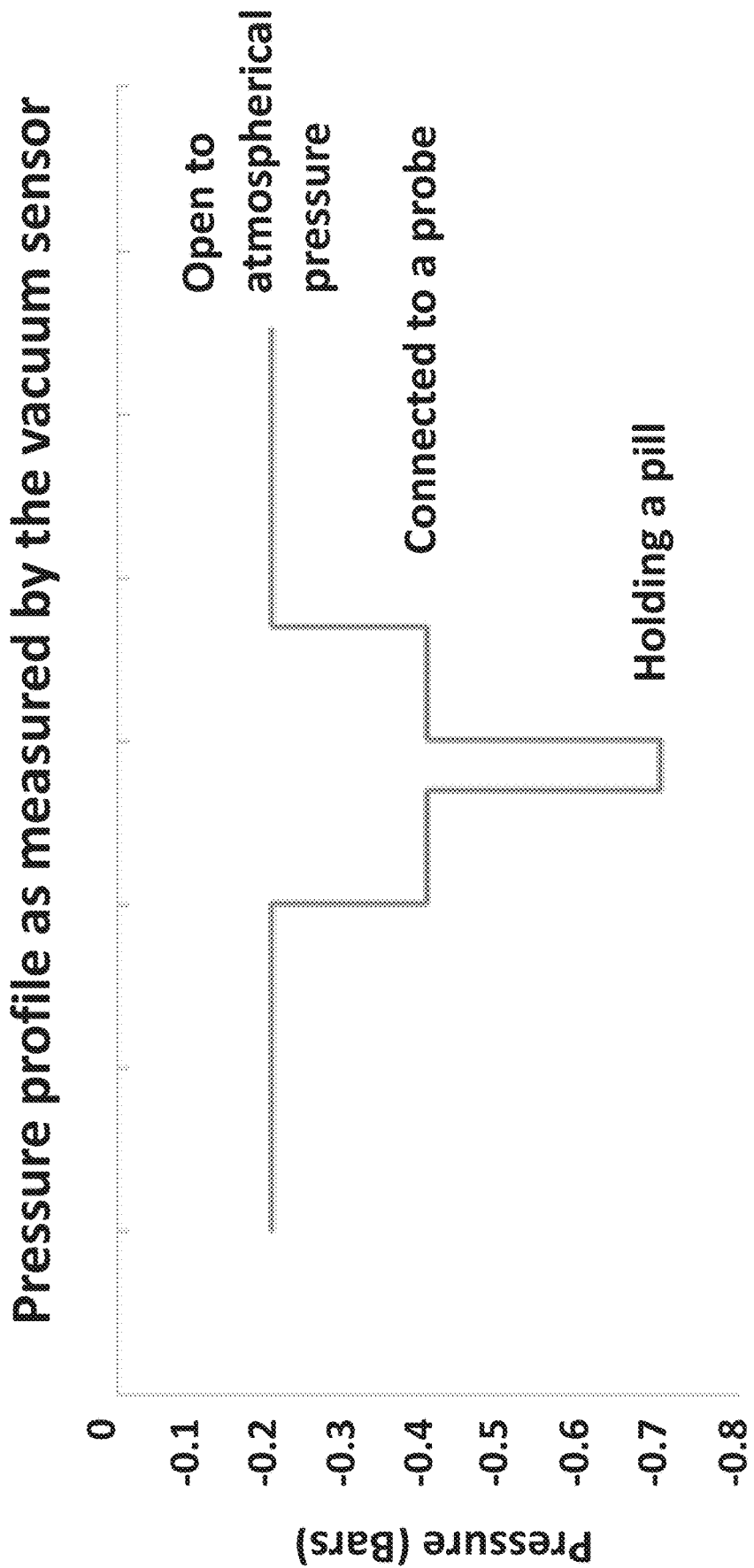
Figure 11:
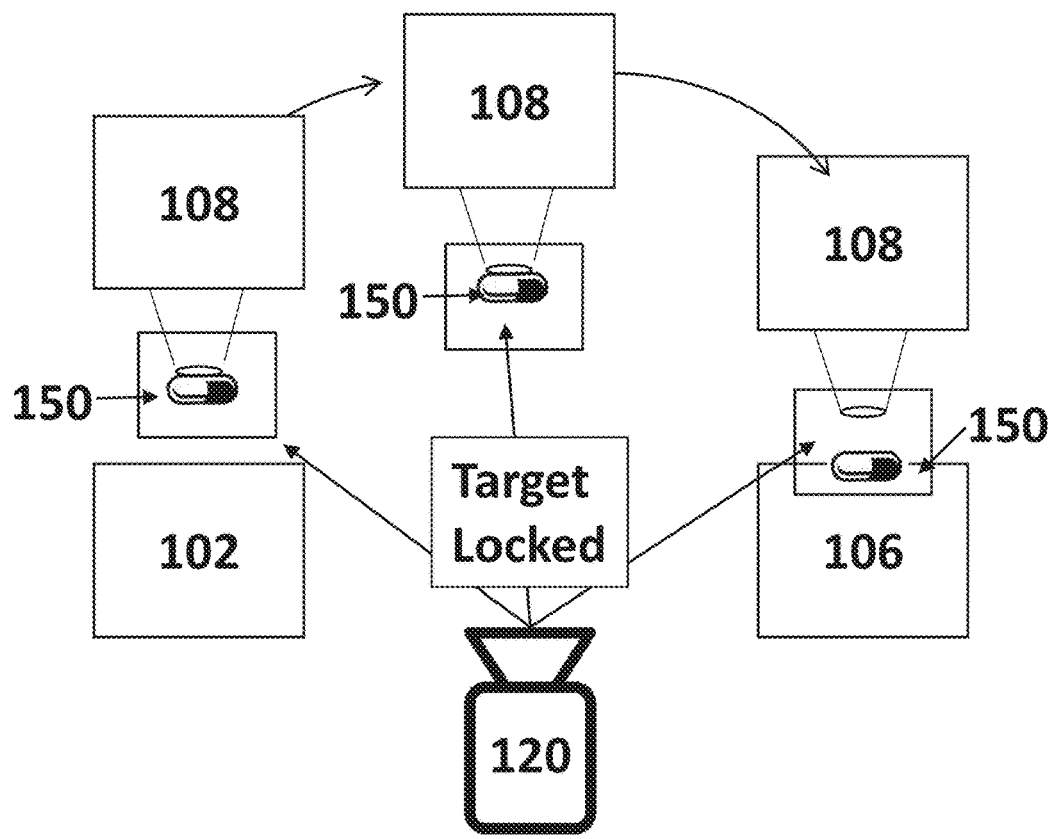
Figure 12:
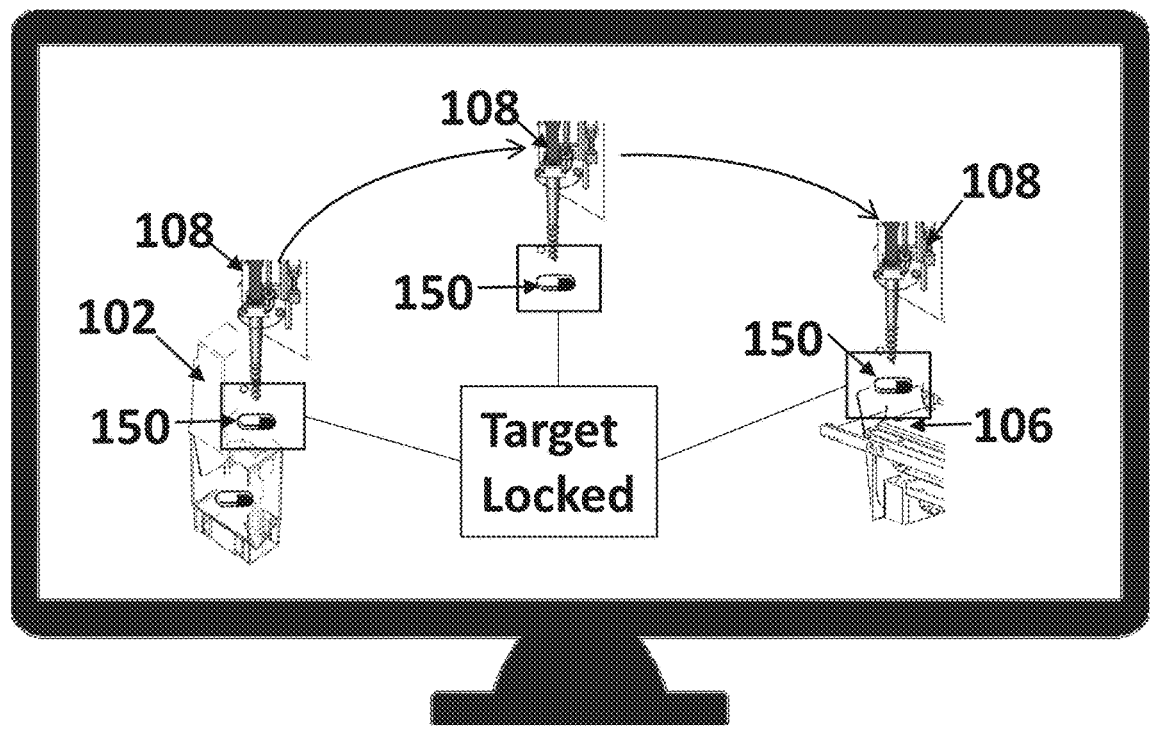
Figure 14:
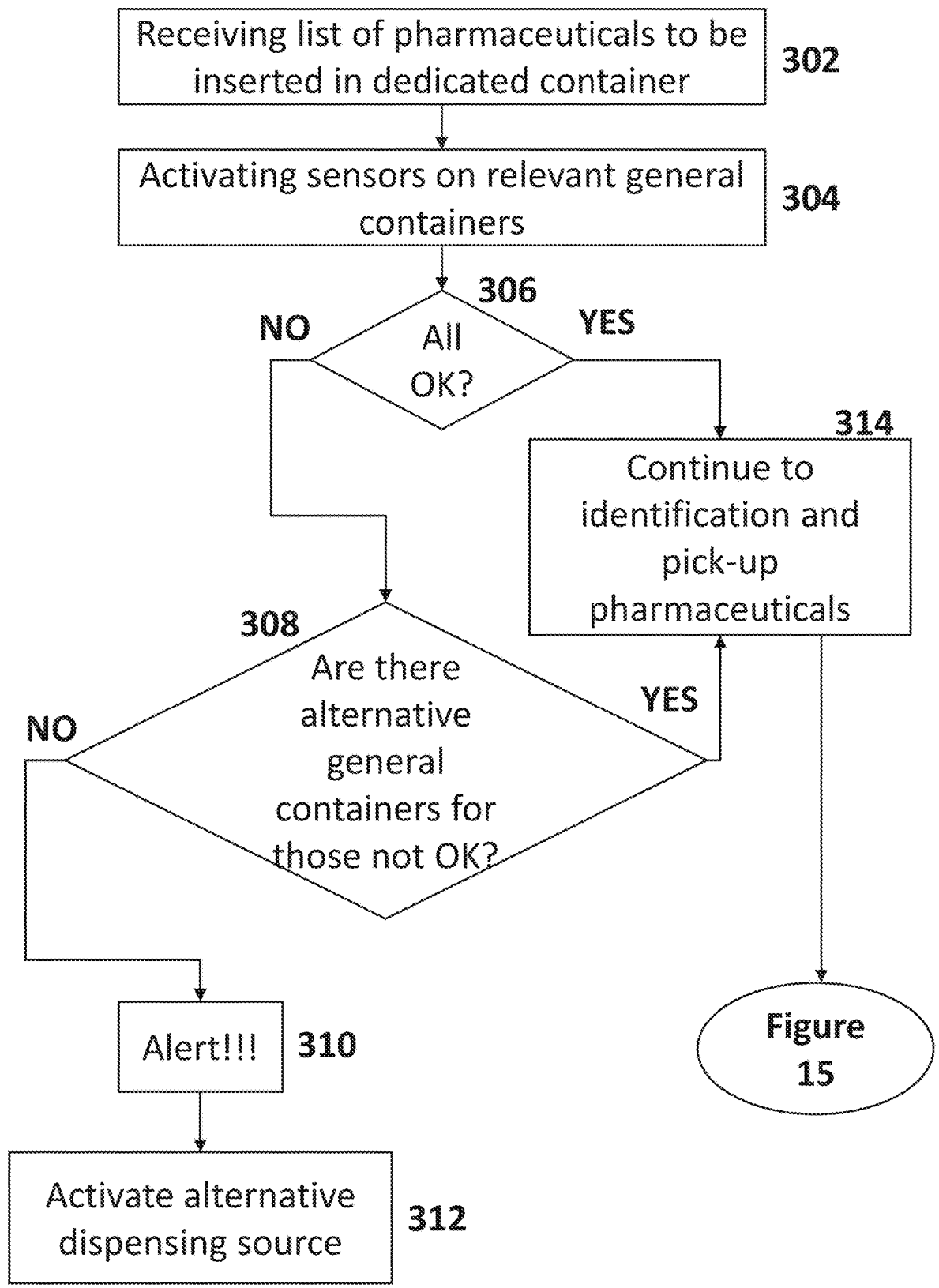

FIGS. 4A-B are schematic illustrations of exemplary pickup elements comprising one or more sensors, according to some embodiments of the invention;

FIG. 5 is an illustration of an exemplary pickup element comprising one or more sensors and that utilizes vacuum for picking pharmaceuticals, according to some embodiments of the invention;

FIG. 6 is a schematic illustration of an exemplary dedicated container, an element holding the dedicated container and one or more sensors, according to some embodiments of the invention;

FIG. 7A is an illustration of an exemplary general container in the form of an envelope and a dedicated container holding element comprising one or more sensors, according to some embodiments of the invention;

FIG. 7B is another illustration of an exemplary general container in the form of an envelope and a dedicated container holding element comprising one or more sensors, according to some embodiments of the invention;

FIG. 8 is a schematic diagram of an exemplary vacuum system, according to some embodiments of the invention;

FIG. 9 is a schematic diagram of another exemplary vacuum system, according to some embodiments of the invention;

FIG. 10 is a schematic pressure graph as measured by a vacuum sensor, according to some embodiments of the invention;

FIG. 11 is a schematic representation of video monitoring process, according to some embodiments of the invention;

FIG. 12 is a schematic representation of video monitoring process watched remotely, according to some embodiments of the invention;

FIG. 13 is a schematic representation of video monitoring process for pharmaceutical labels used in dedicated pharmaceutical containers and/or video monitoring process for printed information on the dedicated pharmaceutical containers, according to some embodiments of the invention; and FIGS. 14, 15, 16, 17, 18, 19 and 20 are flowchart of exemplary methods, according to some embodiments of the invention.

DESCRIPTION OF SPECIFIC EMBODIMENTS OF THE INVENTION

The present invention, in some embodiments thereof, relates to apparatuses and methods for sensors used in packaging and dispensing machines and, more particularly, but not exclusively, to apparatuses and methods for dedicated sensors used in pharmaceutical packaging and dispensing machines.

Overview

An aspect of some embodiments of the invention relates to monitoring performance during pharmaceutical dispensing processes performed by pharmaceutical dispensing machines. In some embodiments, monitoring performance during a pharmaceutical dispensing process potentially allows to guarantee one or more of dispensing the correct pharmaceuticals to the users, the correct performance of the pharmaceutical dispensing machine, reduction of unnecessary discard of pharmaceuticals due to technical issues, standing to governmental regulatory requirements. In some embodiments, monitoring includes monitoring the location and/or movement of a pharmaceutical. In some embodiments, monitoring includes monitoring performance of individual components of the pharmaceutical dispensing device. In some embodiments, monitoring includes monitoring sounds emitted by the pharmaceutical dispensing device and/or inside the pharmaceutical dispensing device and/or outside the pharmaceutical dispensing device. In some embodiments, monitoring includes visually and/or optically and/or digitally monitoring the pharmaceutical dispensing process. In some embodiments, monitoring is performed in real-time during the pharmaceutical dispensing process and/or before commencing the pharmaceutical dispensing process and/or after the end of the pharmaceutical dispensing process. In some embodiments, monitoring is performed using one or more sensors. In some embodiments, one or more sensors are one or more of movement sensor, weight sensor, infrared sensor, vibration sensor, sound sensor, vacuum sensor, video device. In some embodiments, monitoring includes comparing the information received from the one or more sensors and compared with information in a database. In some embodiments, the information recovered by the one or more sensors is sent to a server and saved for future reference. In some embodiments, detection of problems causes the pharmaceutical dispensing machine to contact a server and/or dedicated personnel. In some embodiments, detection of problems causes the pharmaceutical dispensing machine to activate alternative pharmaceutical dispensing sources, for example other pharmaceutical dispensing devices and/or a pharmacy.

An aspect of some embodiments of the invention relates to monitoring one or more of the different parts in a pharmaceutical dispensing machine, pharmaceuticals being moved inside a pharmaceutical dispensing machine and dedicated containers comprising pharmaceuticals to be dispensed to one or more users during a pharmaceutical dispensing process performed by a pharmaceutical dispensing machine. In some embodiments, different parts in a pharmaceutical dispensing machine comprise vacuum elements used during the pharmaceutical dispensing processes performed by the pharmaceutical dispensing machines. In some embodiments, monitoring comprises comparing detected data received from one or more sensors with expected data located in a database. In some embodiments, detection performed by one or more sensors is performed before and/or during and/or after the pharmaceutical dispensing process. In some embodiments, the pharmaceutical dispensing machine is configured to record and update the database with new detected data from the one or more sensors.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

General Introduction

In some embodiments, a pharmaceutical dispensing device comprises a plurality of sensors, for example an optical sensor and/or acoustical sensor, a camera, an optical gate, an infrared camera or microphone, are located inside the pharmaceutical dispensing device. In some embodiments, the sensors are configured to monitor the overall device operations. In some embodiments, monitoring comprise one or more of:

Monitoring the dispensing process and identify a deviation from a programed operation.

Monitoring the device temperature using for example infrared imaging and/or using an array of thermometers located inside the pharmaceutical dispensing machine.

Monitoring the sounds emitted from and by the device and identify deviations from the expected operation sounds.

Monitoring errors in drug dispensing actions by detection of pills fall or drugs spill off out of the pharmaceutical containers.

Monitoring proper handling of the pharmaceutical containers, for example monitoring the opening of the pharmaceutical containers during the filling and/or the container orientation and quality.

In some embodiments, the sensor is an operation sensor that monitors the performances of the pharmaceutical dispensing machine. In some embodiments, such sensors are one or more of: vacuum level sensors, impedance sensors, temperature sensors, pressure sensors, vibration sensor, accelerometer sensors and humidity sensors.

In some embodiments, the sensors are used for one or more of the following general tasks:

Checking if vacuum levels are according to the planed levels. In some embodiments, a deviation from the set values can result in improper container handling. In some embodiments, where the container is an envelope, low vacuum levels can result in envelope drops and/or non-optimal opening of the envelope before placing the drugs inside.

Checking the device electrical circuit status using for example impedance testing between set points in the electrical circuit.

Supervising and monitoring changes in temperature and/or pressure values from normal values. In some embodiments, a deviation can indicate suboptimal device operations.

Checking if vibration levels are above and/or below set values. In some embodiments, this can be an indication for one or more of: a problem in the dynamic operation of the device, lack of proper lubrication between elements and/or improper setting by the operator.

In some embodiments, a controller, comprising a memory storing indication of information regarding expected values data that should be received from the plurality of sensors during a pharmaceutical dispensing process, received the data from the plurality of sensors, and the controller comprises instructions to compare the received data from the sensors with the expected data, and, in case of a discrepancy, alert the necessary personnel.

Figure 1:
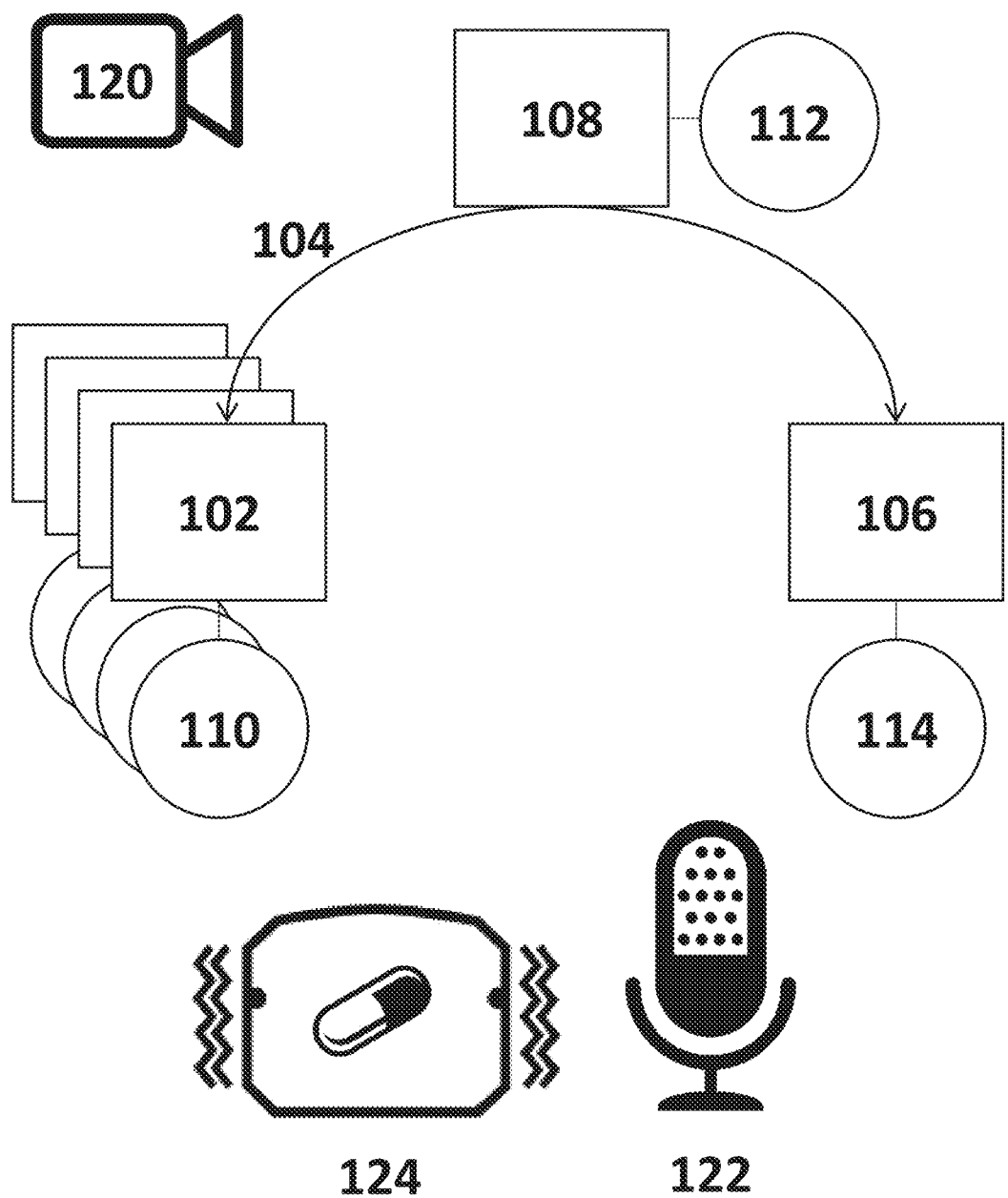
FIG. 1 is a flowchart of an exemplary general method of pharmaceutical dispensing packaging, according to some embodiments of the invention.

Referring now to FIG. 1, showing a flowchart of an exemplary general method of pharmaceutical dispensing packaging, according to some embodiments of the invention. In some embodiments, the principal action of packaging pharmaceuticals to be dispensed comprises picking up one or more pharmaceuticals from one or more containers 102 comprising the one or more pharmaceuticals and moving them 104 into a dedicated container 106 to be dispensed. In some embodiments, the one or more pharmaceuticals are different pharmaceuticals that need to be picked from different general containers. In some embodiments, the movement of pharmaceuticals from one container to another is performed by a dedicated transportation element 108 configured to pick up pharmaceuticals from a general container 102 and move them 104 into dedicated containers 106 to be dispensed. In some embodiments, dedicated sensors (110, 112, 114) are located at each part of the packaging process to monitor the parts and performance of each part to potentially guarantee the correct performance of each part and potentially guarantee a successful pharmaceutical dispensing packaging process. In some embodiments, the pick-up of pharmaceuticals is picking up single pharmaceuticals and/or pills each time. In some embodiments, besides the dedicated sensors located in each part of the pharmaceutical dispensing machine, additional sensors are used in the machine to monitor the general performance of the device, as will be described below. A potential advantage of this is saving money on failed packaged pharmaceuticals, guaranteeing a correct dispensing of pharmaceuticals to the patients.

In some embodiments, the plurality of sensors can monitor a plurality of actions related to the pharmaceutical dispensing process, for example, picking up of the pharmaceutical/pill, movement of the pharmaceutical/pill from a general container to a dedicated container, correct opening and closing of the dedicated container, correct placement of pharmaceutical inside the dedicated container, correct number and/or type of pharmaceuticals/pills placed inside the dedicated container, detection of pharmaceuticals/pills in unexpected locations, correct movement of dedicated container throughout the pharmaceutical dispensing machine from the location of batches of dedicated containers, to the vicinity of the pharmaceuticals in the general containers to the waiting location inside the pharmaceutical dispensing machine.

It should be understood that the sensors monitor activity and send sensed information data values to the controller, which comprises instructions to compare the sensed data values with expected data values to monitor discrepancies.

Exemplary Sensors

In some embodiments, exemplary sensors used in the pharmaceutical dispensing machine include one or more of vacuum sensors, acoustical/sound sensors, optical sensors and temperature sensors.

Exemplary Vacuum Sensors

In some embodiments, vacuum sensors are configured to measure vacuum levels generated by the vacuum pump for specific components and/or for the whole system. In some embodiments, valid values are in the range from about 0.1 Bar to about 1.5 Bar. Optionally from about 0.3 Bar to about 0.9 Bar. Optionally from about 0.5 Bar to about 0.8 Bar. For example 0.1 Bar, 0.2 Bar, 0.3 Bar, 0.4 Bar, 0.5 Bar, 0.6 Bar, 0.7 Bar, 0.8 Bar, 0.9 Bar.

Exemplary Acoustic Sensors

In some embodiments, acoustic sensors are configured to measure sounds emitted by the device and/or sounds not related by the functioning of the device. In some embodiments, the acoustic sensors are configured to measure sounds in the entire spectrum, meaning audio, ultrasonic, and infrasonic. In some embodiments, the acoustic sensors are configured to measure sounds in the audio range, which falls between 20 Hz and 20,000 Hz. In some embodiments, the acoustic sensors are configured to measure sounds in the ultrasonic range, which refers to the very high frequencies: 20,000 Hz and higher. In some embodiments, the acoustic sensors are configured to measure sounds in the infrasonic range, which are frequencies lower than 20 Hz.

Exemplary Optical Sensors

In some embodiments, optical sensors are configured to detect dysfunctions and/or anomalies in the operation of the device. In some embodiments, the device uses a baseline video recording of the device during proper device operation used to compare with real-time video recordings of the operation of the device and detect the anomalies. In some embodiments, the image can be infrared imaging of the device, indicating a temperature value of the internal temperature of the device. In some embodiments, images and/or video sequences are analyzed only when un-normal sounds are detected or other "suspected" signals are received from an array of other sensors.

Exemplary Temperature Sensors

In some embodiments, the device comprises one or more temperature sensors configured to measure the internal temperature of the device in general and the temperature of the general pharmaceutical containers that storage the pharmaceuticals. In some embodiments, the device monitors the correct functioning of the device by monitoring the temperature. In some embodiments, the temperature should not be over for example 25 degrees Celsius, optionally not over 30 degrees Celsius, optionally not over 35 Degrees Celsius. In some embodiments, the temperature should not be below for example 4 degrees Celsius, optionally not below 10 degrees Celsius, optionally not below 15 Degrees Celsius. In some embodiments, when temperature is above and/or below a set threshold the system exchanges air with the surrounding area to help achieve the set temperature.

Exemplary Sensors in General Containers

Figure 2:
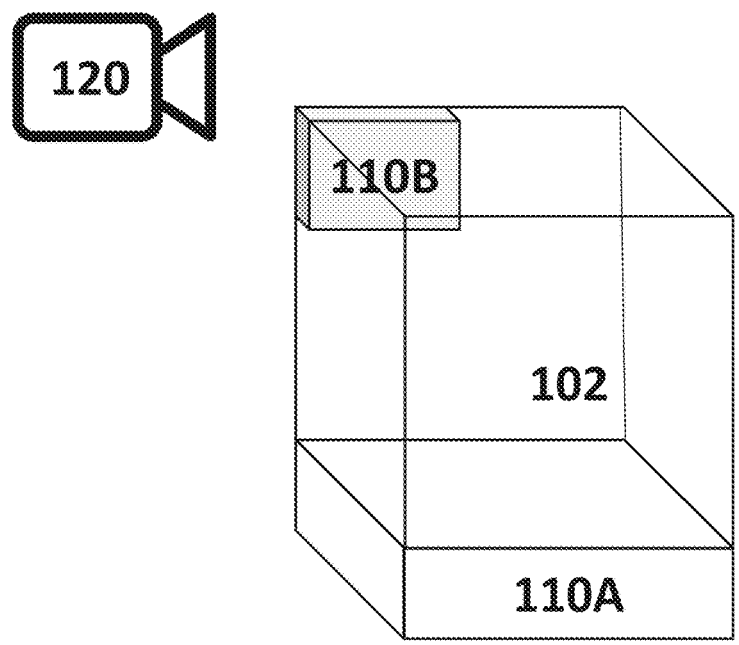
FIG. 2 is a schematic illustration of an exemplary general container comprising one or more sensors, according to some embodiments of the invention.

Referring now to FIG. 2, showing a schematic illustration of an exemplary general container comprising one or more sensors, according to some embodiments of the invention. In some embodiments, general containers 102 comprising a single type of pharmaceuticals comprise one or more sensors 110A/110B configured to monitor one or more of:

The quantity of pharmaceuticals in the general container. For example, the general container comprises a weight sensor 110A configured to calculate the weight of the contents in the general container. In some embodiments, knowing the type of pharmaceutical, the weight of each pharmaceutical and the initial number of pharmaceuticals in the general container provides the system with the initial weight in the container. In some embodiments, after each dispensing process, each sensor in each container that pharmaceuticals were taken from will control the actual weight of the container, which will ensure that pharmaceuticals were taken and/or that the right number of pharmaceuticals were taken.

The atmospheric environment of the pharmaceuticals. For example, the general container comprises one or more of a temperature sensor, a humidity sensor, a light sensor, or a combination thereof 110B, configured to monitor the environmental conditions on which the pharmaceuticals are kept.

Figure 3:
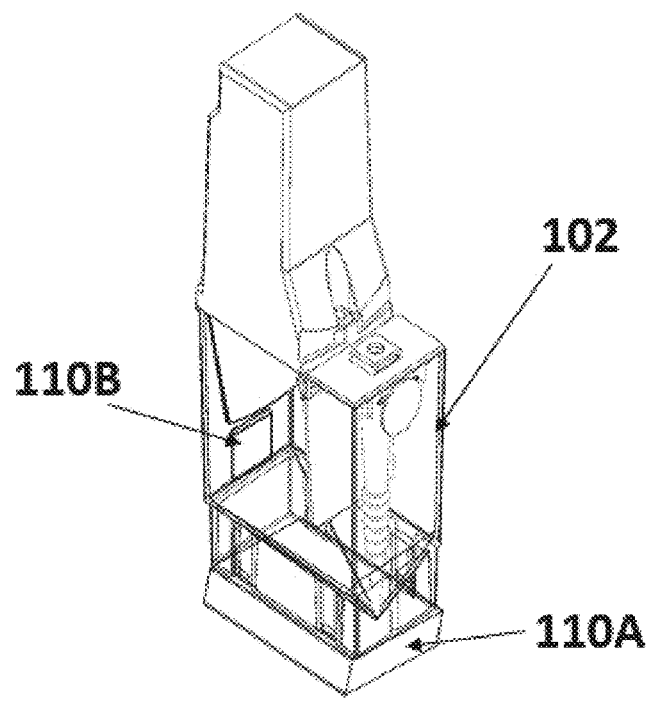
FIG. 3 is an illustration of an exemplary general container comprising one or more sensors, according to some embodiments of the invention.

Referring now to FIG. 3, showing an illustration of an exemplary general container comprising one or more sensors, according to some embodiments of the invention. As shown in FIG. 2, in some embodiments, general containers 102 comprising a single type of pharmaceuticals comprise one or more sensors 110A/110B, configured as disclosed above.

Exemplary Sensors in Pick-Up Element

Referring now to FIGS. 4A-B, showing a schematic illustrations of exemplary pickup elements comprising one or more sensors, according to some embodiments of the invention. In some embodiments, pickup element 108 configured to pick up any type of pharmaceuticals comprise one or more sensors 112A/112B/112C configured to monitor one or more of:

The positive acquisition of a pharmaceutical. For example, in some embodiments, when the pickup element comprises a scoop-like element, the scoop-like compartment comprises an acoustic sensor and/or an infrared sensor for volume analysis 112A configured to identify that a pharmaceutical 150 has been picked, and optionally also how many pharmaceuticals have been picked, as shown for example in FIG. 4A. In some embodiments, knowing the volume of the type of pharmaceutical provides the system with the expected volume that should be sensed. Another example, in some embodiments, when the pickup element utilizes vacuum to single pick pharmaceuticals, the pickup element comprises a suction sensor 112B configured to sense when a pharmaceutical has been picked, as shown for example in FIG. 4B.

The movement perform by the pickup element. In some embodiments, for example, the pickup element moves from location to another, for example, from a general container to a dedicated container. In some embodiments, the pickup element comprises a gyroscope 112C configured to sense the movements performed by the pickup element and register any malfunction in the expected moves of the pickup element, as shown for example in FIGS. 4A-B.

Referring now to FIG. 5, showing an illustration of an exemplary pickup element comprising one or more sensors and that utilizes vacuum for picking pharmaceuticals, according to some embodiments of the invention. As shown in FIG. 4B, in some embodiments, the pickup element 108 comprises one or more sensors 112B, configured as disclosed above.

It should be noted that since, in some embodiments, the pharmaceutical is picked up by the pickup element by means of vacuum (as shown for example in FIGS. 4B and 5), there is a possibility that the pharmaceutical can fall during the movement of the pharmaceutical from one location to another, for example, due to a problem in the vacuum system.

Exemplary Pharmaceutical Identification/Verification

In some embodiments, pickup element 108 is configured to communicate with the general containers 102 via a chip or RFID tag mounted at the container, or by using barcode at the container. In some embodiments, the RFID/chip is used to transmit operational parameters of the container. Some examples of information that can be communicated via RFID/chip are: identifying medication within container, counting medication dosages, receiving status details, dispensing status, etc. In some embodiments, pickup element 108 is configured to transmit updated information encoded on the container to a server. For example: updating medication dosage remaining within container after extraction. In some embodiments, pickup element 108 comprises a RFID/tag reader and/or encoder. In some embodiments, the reader/encoder is movable to enable approximating and detracting to/from the general containers 102. In some embodiments, the reader/encoder is configured to move together with pickup element 108. For example, for approximating RFID tag/Chip of general containers 102, while picking a probe. In some embodiments, the communication of pickup element 108 with general containers 102 is used to avoid an initiation of medication extraction in case the reader/encoder detects some unexpected input from a chip of the general containers 102, e.g. out of medication/wrong medication. In some embodiments, such unexpected inputs causes the pickup element 108 to move to the next general container 102, without proceeding a faulty dispensing process.

A potential advantage of this is the potentially increased usability by reducing faulty handling by an operator, and the potentially reduction of idling of the dispensing system.

Exemplary Sensors in Dedicated Containers

Referring now to FIG. 6, showing a schematic illustration of an exemplary dedicated container, an element holding the dedicated container and one or more sensors, according to some embodiments of the invention. In some embodiments, dedicated containers 106 are used to collect one or more pharmaceuticals 150 to be dispensed to patients. In some embodiments, once the dedicated container 106 is filled, it is then closed and labeled. In some embodiments, a dedicated container holding element 116 is used to hold and manipulate the dedicated container during the pharmaceutical dispensing process. In some embodiments, manipulation comprises one or more of picking up a dedicated container from a dedicated container storage, holding the dedicated container during the pharmaceutical dispensing process, opening the dedicated container and closing the dedicated container after all necessary pharmaceutical have been inserted. In some embodiments, the dedicated container holding element 116 comprises one or more sensors configured to monitor the manipulation of the dedicated container 106 during the pharmaceutical dispensing process. In some embodiments, monitoring comprises one or more of:

The quantity of pharmaceuticals in the dedicated container. For example, the dedicated container holding element 116 comprises a weight sensor 114A configured to calculate the weight of the contents in the dedicated container. In some embodiments, knowing the type of pharmaceutical, the weight of each pharmaceutical and the final number of pharmaceuticals that need to be inserted in the dedicated container provides the system with the final weight in the container, which can be compared with the actual weight once all necessary pharmaceuticals are deposited in the dedicated container. In some embodiments, measuring the final weight can potentially confirm that the right type of pharmaceuticals and the right number of pharmaceutical were deposited in the dedicated container.

The positive insertion of pharmaceuticals. For example, in some embodiments, when the pharmaceutical is dropped into the dedicated container, an acoustic sensor and/or an infrared sensor for volume analysis 114B configured to measure and identify how many and which pharmaceuticals have been dropped into the dedicated container. In some embodiments, knowing the volume of the type of pharmaceutical provides the system with the expected volume that should be sensed.

The positive manipulation of the dedicated container. For example, the same and/or another acoustic sensor and/or an infrared sensor and/or vacuum sensor are used to evaluate that the dedicated container has been correctly handled. In some embodiments, handling the dedicated container comprises one or more of picking up a dedicated container, opening a dedicated container, closing a dedicated container, moving dedicated containers from one point to another.

Referring now to FIG. 7A, showing an illustration of an exemplary dedicated container in the form of an envelope 118 and a dedicated container holding element 116 comprising one or more sensors, according to some embodiments of the invention. As shown in FIG. 6, in some embodiments, dedicated container holding element 116, which are configured to hold the dedicated containers, comprises one or more sensors 114A/114B, configured as disclosed above.

Referring now to FIG. 7B, showing an illustration of an exemplary dedicated container in the form of an envelope 118 and a dedicated container holding element 116 comprising one or more sensors, according to some embodiments of the invention. In some embodiments, the pharmaceutical dispensing system comprises one or more sensors 130-132a-c configured to monitor the correct opening and closing of the envelope. In some embodiments, a potential advantage of monitoring the correct opening and closing of the envelope is the potential reduction of the number of faulty tries of delivery of pharmaceuticals into the envelopes and/or potential increment in successful filled envelopes.

In some embodiments, the dedicated container holding element 116 comprises a sensor 130 (optionally an optical sensor) configured to measure the presence of a dedicated container, for example an envelope. In some embodiments, when the envelope is present, the beam of the sensor contacts the envelope, thereby signaling a positive signal of the presence of the envelope. In some embodiments, when the envelope is not present or is present in a faulty way, the beam of the sensor will either not contact the envelope or will contact the envelope in a non-expected manner, thereby signaling a negative signal.

In some embodiments, the dedicated container holding element 116 comprises a sensor 132a-c (optionally a through-beam sensor), comprising a transmitter 132a and a receiver 132b, in which a through-beam 132c is activated. In some embodiments, the sensor 132a-c is configured to detect disturbance in the through-beam 132c. In some embodiments, when the envelope is opened to receive a pharmaceutical and/or when the envelope receives a pharmaceutical, a "belly" is form from the opening of the envelope and/or from the pharmaceutical inside the envelope. In some embodiments, when the "belly" is formed, the "belly" interrupts the through-beam 132c, thereby signaling the correct opening of the envelope and/or the correct insertion of a pharmaceutical inside the envelope.

In some embodiments, the envelope status is further monitored by a vacuum system, as described below.

Exemplary Vacuum Systems and Sensors Thereof

In some embodiments, one or more parts of the system utilizes vacuum to perform the tasks of the pharmaceutical dispensing methods. In some embodiments, vacuum is used for the manipulation of the dedicated container, which comprises one or more of picking up the dedicated container, opening the dedicated container, closing the dedicated container, moving the dedicated container from one location to another. In some embodiments, vacuum is used for the manipulation of pharmaceuticals, which comprises one or more of picking a pharmaceutical, holding a pharmaceutical while is being moved, dropping a pharmaceutical. In some embodiments, the system comprises one or more vacuum sensors configured to monitor the vacuum levels, optionally at specific locations, which provide indications of correct and/or incorrect functionality of the vacuum during the pharmaceutical dispensing methods. In some embodiments, deviation in set vacuum values may indicate a problem, for example loss of a pharmaceutical, improper opening of a dedicated container, etc.

Referring now to FIG. 8, showing a schematic diagram of an exemplary vacuum system, according to some embodiments of the invention. In some embodiments, the vacuum system comprises a vacuum pump 202 configured to provide the necessary vacuum to the system. In some embodiments, the vacuum system comprises a plurality of valves 206 configured to open and/or close vacuum elements when necessary. In some embodiments, the vacuum pump 202 comprises a vacuum sensor 204 configured to measure the vacuum levels for whole system as generated by the vacuum pump. In some embodiments, valid values are in the range of −0.4 (minimal value when all valves are open) and up to −0.9 bars (when all valves are closed), Typical operation value is in the range of −0.7 bar. In some embodiments, the dedicated container holding element 116 comprises a vacuum element configured to pick up a dedicated container, for example an envelope 208. In some embodiments, the vacuum element of the dedicated container holding element 116 comprises a vacuum sensor 210 configured to measure the vacuum levels for the vacuum element responsible for picking up the envelopes. In some embodiments, valid vacuum values for this vacuum element are in the range of −0.7 bar during periods where the vacuum tip hold the envelope and −0.2 bar when the vacuum tip is open. In some embodiments, the vacuum system comprises a vacuum element configured to open the envelopes 208, referred hereinafter as envelope opener 212. In some embodiments, the envelope opener 212 comprises an optical sensor 120 configured to detect the correct opening of the envelopes 208. In some embodiments, the system comprises a vacuum element configured to pick up pharmaceuticals, referred hereinafter as "pills probe" 216, and a vacuum element configured to hold the envelope while is being moved inside the machine, referred hereinafter as "head envelope" 218. In some embodiments, optionally, both vacuum elements for picking up pharmaceuticals 216 and for holding the envelopes 218 are located in the same location, for example on a head module 214. In some embodiments, the head module 214 is moved around the device to reach specific general pharmaceutical containers. In some embodiments, the head envelope 218 comprises a vacuum sensor 220 configured to measure the vacuum levels for the head envelope 218. In some embodiments, valid vacuum values for the head envelope 218 vacuum sensor 220 are in the range of −0.7 bar during periods where the vacuum tip hold the envelope and −0.2 bar when the vacuum tip is open. In some embodiments, the pills probe 216 comprises a vacuum sensor 222 configured to measure the vacuum levels for the pills probe 216. In some embodiments, valid vacuum values for the pills probe 216 vacuum sensor 222 are in the range of −0.7 bar during periods where the tip hold the pill, −0.3--0.4 bar when the pills probe is connected to the moving head and −0.2 bar when the vacuum tip is open without the probe. In some embodiments, higher pressure values or lower pressure values may indicate that the filter connected to the valve is not working properly.

Referring now to FIG. 9, showing a schematic diagram of another exemplary vacuum system, according to some embodiments of the invention. In some embodiments, larger pharmaceutical dispensing machines may comprise double or triple parallel valves and/or vacuum elements and/or vacuum sensors, configured to allow parallel dispensing processes at the same time and/or to allow bypass of one vacuum element to use another incase the first one does not work properly. Besides the same parts shown in FIG. 8, in FIG. 9 is also shown an air compressor 224 configured to provide pressure to a pressure tank 226. In some embodiments, the pressure tank comprises a pressure sensor 228 configured to measure pressure in the pressure tank 226. In some embodiments, the pressure tank 226 is used for controlling the pressure nozzle 230 that is used for envelope opening 212. Alternatively, the pressure tank 226 is used to increase the pressure through certain blocked vacuum pipes in order to open them in case of blockage (referred as "blowing through the pipes"). In some embodiments, valid vacuum values for the pressure tank 226 vacuum sensor 228 are in the range of 0.1-2 bar.

Referring now to FIG. 10, showing a schematic graph of a pressure profile comprising a plurality of predetermined sequential pressure values, according to some embodiments of the invention. In some embodiments, the pharmaceutical dispensing machine comprises instructions to follow a determined number of actions when relaying the pharmaceutical from one location to another when using the vacuum system. In some embodiments, each action is characterized by a certain pressure value that can be detected by the vacuum sensor. For example, as shown in FIG. 10, when nothing is attached to the vacuum system, the vacuum sensor detects a pressure of about −0.2 Bars, while when a probe is connected to the vacuum system, the vacuum sensor detects a pressure of about −0.4 Bars. Lastly, when a pharmaceutical is picked by the vacuum system using a probe, the vacuum sensor detects a pressure of about −0.7 Bars. In some embodiments, the pressure detected by the vacuum sensor when nothing is attached to it is from about −0.1 Bars to about −0.3 Bars, with a deviation of about ±0.05 Bars. In some embodiments, the pressure detected by the vacuum sensor when the probe is attached to it is from about −0.3 Bars to about −0.6 Bars, with a deviation of about ±0.05 Bars. In some embodiments, the pressure detected by the vacuum sensor when a pharmaceutical is attached to the probe is from about −0.6 Bars to about −0.8 Bars, with a deviation of about ±0.05 Bars. In some embodiments, the plurality of pressure values in a determined sequential order provides a pressure profile. In some embodiments, a predetermined pressure profile is used to instruct the pharmaceutical dispensing machine on how to transport a pharmaceutical from one location to another. In some embodiments, the pharmaceutical dispensing machine utilizes the detection of the pressure values/pressure profile to monitor the correct relaying of a pharmaceutical. In some embodiments, deviations from the expected detection of the pressure profile indicates a problem in the relaying process of the pharmaceutical.

In some embodiments, the pharmaceutical dispensing system comprises a database having information regarding an expected pressure profile comprising a plurality of predetermined sequential pressure values unique for each pharmaceutical. In some embodiments, each pharmaceutical expected pressure profile is different to another due to, for example, the size of the pharmaceutical and/or the form of the pharmaceutical.

In some embodiments, when a new pharmaceutical is added to a pharmaceutical dispensing machine, and there is no expected pressure profile comprising a plurality of predetermined sequential pressure values in record for that new pharmaceutical, the pharmaceutical dispensing machine records the actual pressure profile comprising the plurality of actual sequential pressure values recorded during the relaying process and it adds it to the database for future references.

Exemplary Video Monitoring in Pharmaceutical Dispensing Machines

Referring back to FIG. 1, showing a flowchart of an exemplary method of pharmaceutical dispensing packaging, according to some embodiments of the invention. In some embodiments, the pharmaceutical dispensing machine comprises one or more video cameras 120 configured to provide real-time video feed of the pharmaceutical dispensing process occurring in the pharmaceutical dispensing machine. In some embodiments, there is only one video camera configured to capture a general view of the machine. In some embodiments, each component comprises a dedicate video camera configured to monitor the activities of each element. For example, a dedicated video camera is attached to each general container and it is configured to monitor the status of the general container before, during and after pharmaceuticals are picked up from the dedicated container. Another example, a dedicated video camera is attached to the dedicated element 108 configured to pick up pharmaceuticals, and it configured to monitor the pickup actuation of pharmaceuticals. Another example, a dedicated video camera is attached to the dedicated container holding element 116 and it is configured to monitor the insertion of pharmaceuticals into the dedicated container and the correct opening and/or closure of the dedicated container.

Referring now to FIG. 11, showing a schematic representation of video monitoring process, according to some embodiments of the invention. In some embodiments, the video camera 120 is equipped with specialized tracking software configured to identify a pharmaceutical being taken from a general container 102 by a dedicated transportation element 108 into a dedicated container 106. In some embodiments, the software is configured to identify the pharmaceutical being picked, lock on it, and monitor the movement of the pharmaceutical from one to another. In some embodiments, the video feed is monitored and can be watched remotely, as schematically shown for example in FIG. 12.

Referring now to FIG. 13, showing a schematic representation of video monitoring process for pharmaceutical labels used in dedicated pharmaceutical containers and/or video monitoring process for printed information on the dedicated pharmaceutical containers, according to some embodiments of the invention. In some embodiments, each dedicated container is marked with information regarding the specific user that needs to receive the pharmaceuticals. In some embodiments, the information is printed on labels and then attached to the dedicated containers. In some embodiments, the information is directly printed on the dedicated container. In some embodiments, there is video camera that monitors the results of the printing process, as schematically shown for example in FIG. 13. As can be seen, the upper label is correct and the lower label comprises defects created for example due to ending of toner. In some embodiments, the system comprises a dedicated software configured to identify correct labels and defected labels.

Exemplary Sound Sensor in Pharmaceutical Dispensing Machines

Referring back to FIG. 1, showing a flowchart of an exemplary method of pharmaceutical dispensing packaging, according to some embodiments of the invention. In some embodiments, the pharmaceutical dispensing machine comprises one or more sound sensors 122 configured to monitor the sounds emitted by the machine during the pharmaceutical dispensing process. In some embodiments, the system comprises a database of typical sounds produced by the different parts of the system during a typical pharmaceutical dispensing process. In some embodiments, real-time sounds are collected during the pharmaceutical dispensing process and they are compared to baseline sounds stored in the database. In some embodiments, baseline sounds will include one or more of: sounds of the machine working properly, sounds of each element in the machine working properly, sounds of each element not working properly. In some embodiments, identification of unknown sounds and/or identification of a sound of an element not working properly triggers an alert. In some embodiments, the sound sensors are configured to detect the sound of falling objects inside the pharmaceutical dispensing machine, for example, the sound of a pharmaceutical falling inside the machine. In some embodiments, detection of a sound of an object that fell inside the machine triggers an alert.

Exemplary Vibration Sensor in Pharmaceutical Dispensing Machines

Referring back to FIG. 1, showing a flowchart of an exemplary method of pharmaceutical dispensing packaging, according to some embodiments of the invention. In some embodiments, the pharmaceutical dispensing machine comprises one or more vibration sensors 124 configured to monitor the vibrations detected in the machine during the pharmaceutical dispensing process. In some embodiments, the system comprises a database of typical vibrations produced by the different parts of the system during a typical pharmaceutical dispensing process. In some embodiments, real-time vibrations are collected during the pharmaceutical dispensing process and they are compared to baseline vibrations stored in the database. In some embodiments, baseline vibrations will include one or more of: vibrations of the machine working properly, vibrations of each element in the machine working properly, vibrations of each element not working properly. In some embodiments, identification of unknown vibrations and/or identification of a vibration of an element not working properly triggers an alert. In some embodiments, the vibration sensors are configured to detect the vibration created by falling objects inside the pharmaceutical dispensing machine, for example, the vibration produced by a pharmaceutical falling inside the machine. In some embodiments, detection of a vibration of an object that fell inside the machine triggers an alert.

Exemplary Methods

Referring now to FIGS. 14-20, showing flowchart of exemplary methods, according to some embodiments of the invention. In some embodiments, the pharmaceutical dispensing machine receives from the server (or manual insertion of requests) a list of pharmaceuticals to be dispensed to one or more specific users 302. In some embodiments, the list of pharmaceutical are pharmaceuticals that need to be picked up from general containers containing said one or more pharmaceuticals, moved and inserted in one or more dedicated containers, which will be then dispensed to the users. In some embodiments, once the machine is ready to begin the pharmaceutical dispensing process the machine activates the plurality of sensors in the general containers 304 to assess if there is any problem, for example, the general container is empty, the general container is not well connected to the device, the general container suffered an increase and/or decrease in temperature. In some embodiments, the system then assesses the information received from the sensors of the general containers to evaluate if they are "all OK" 306. In some embodiments, if the answer is "no", then the system assesses if there are alternative general containers in the same device that can be used instead of those general containers that were found faulty 308. In some embodiments, if the answer is "no", then the system sends an alert 310 and activates an alternative dispensing source for that specific pharmaceutical 312. In some embodiments, alternative sources may be another pharmaceutical dispensing machine in the same location, another pharmaceutical dispensing machine in a different location, a warehouse and/or a pharmacy. In some embodiments, if the answer is "yes" to "all OK?" 306 and/or to "Are there alternatives?" 308, then the pharmaceutical dispensing machine continues to identify and pick up the required pharmaceuticals 314, which continues in FIG. 15.

Figure 15:
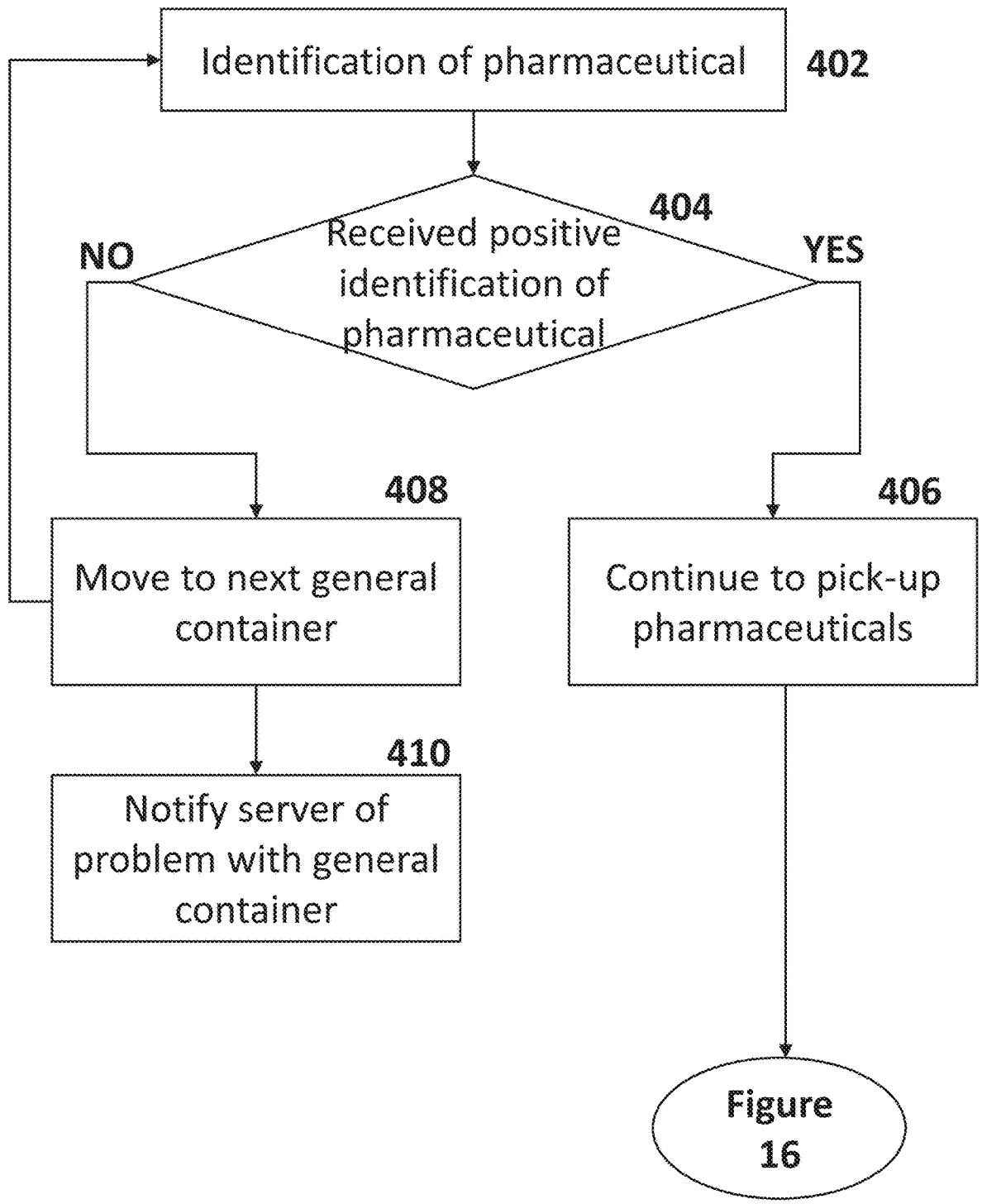

Referring now to FIG. 15, the continuation of a flow chart of an exemplary method, according to some embodiments of the invention. In some embodiments, the dedicated transportation element 108 arrives at the general container 102 and an identification of the pharmaceutical is performed before trying to pick up any pharmaceutical 402. In some embodiments, identification and/or verification and/or transmittal of information is performed as disclosed above and as disclosed in U.S. patent application Ser. No. 16/430,456, which is hereby incorporated herein by reference in its entirety. In some embodiments, the system assesses if a positive identification of the pharmaceutical has been received 404. In some embodiments, if the answer is yes, then the pharmaceutical dispensing machine continues to pick up the required pharmaceuticals 406, which continues in FIG. 16. In some embodiments, if the answer is "no", then the system moves to the next general container 408 and performs again the identification process 402. In some embodiments, furthermore, the pharmaceutical dispensing machine sends an alert 410 to the server notifying that has been a problem with the identification of the pharmaceutical.

Figure 16:
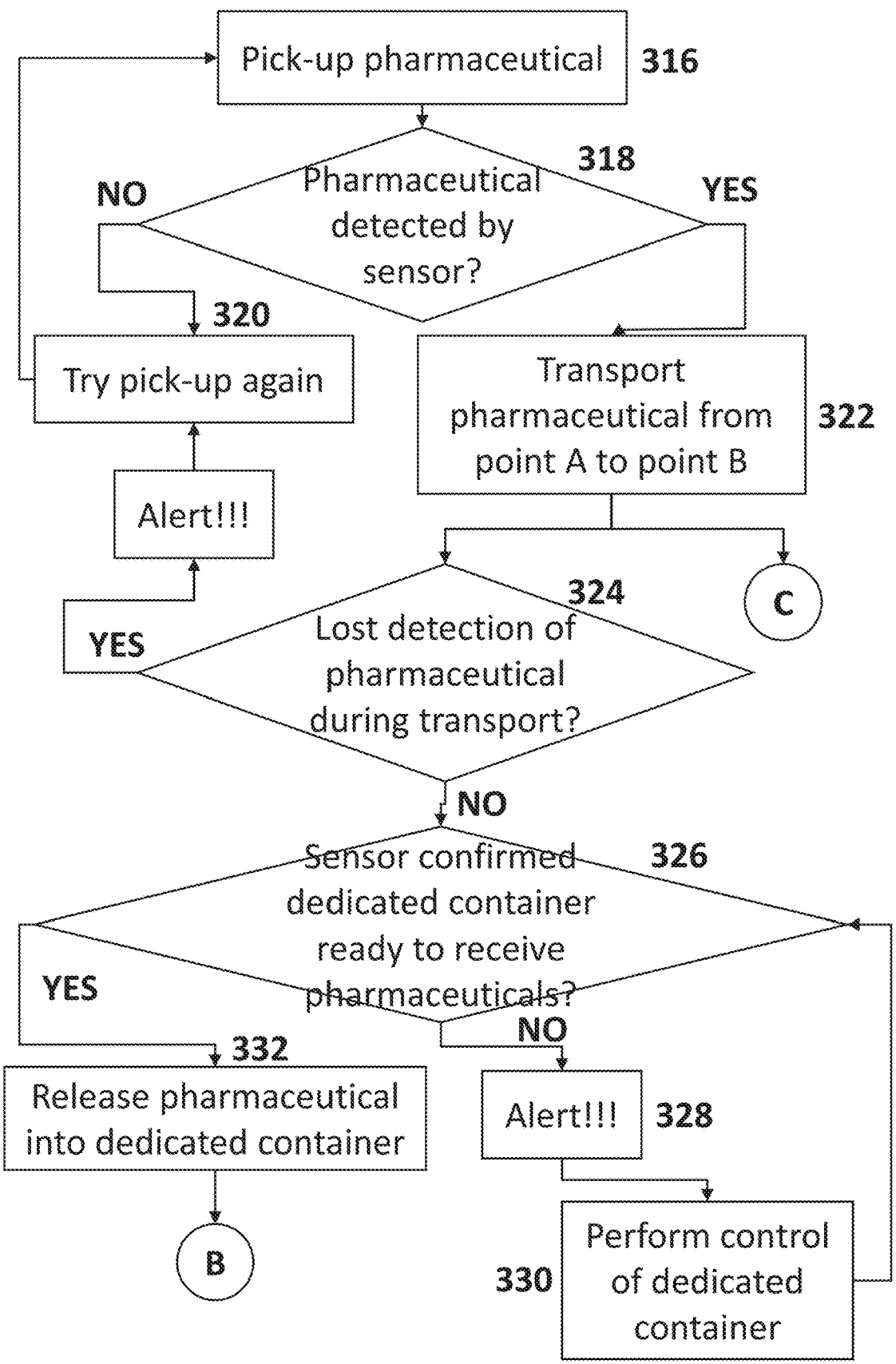
Figure 17:
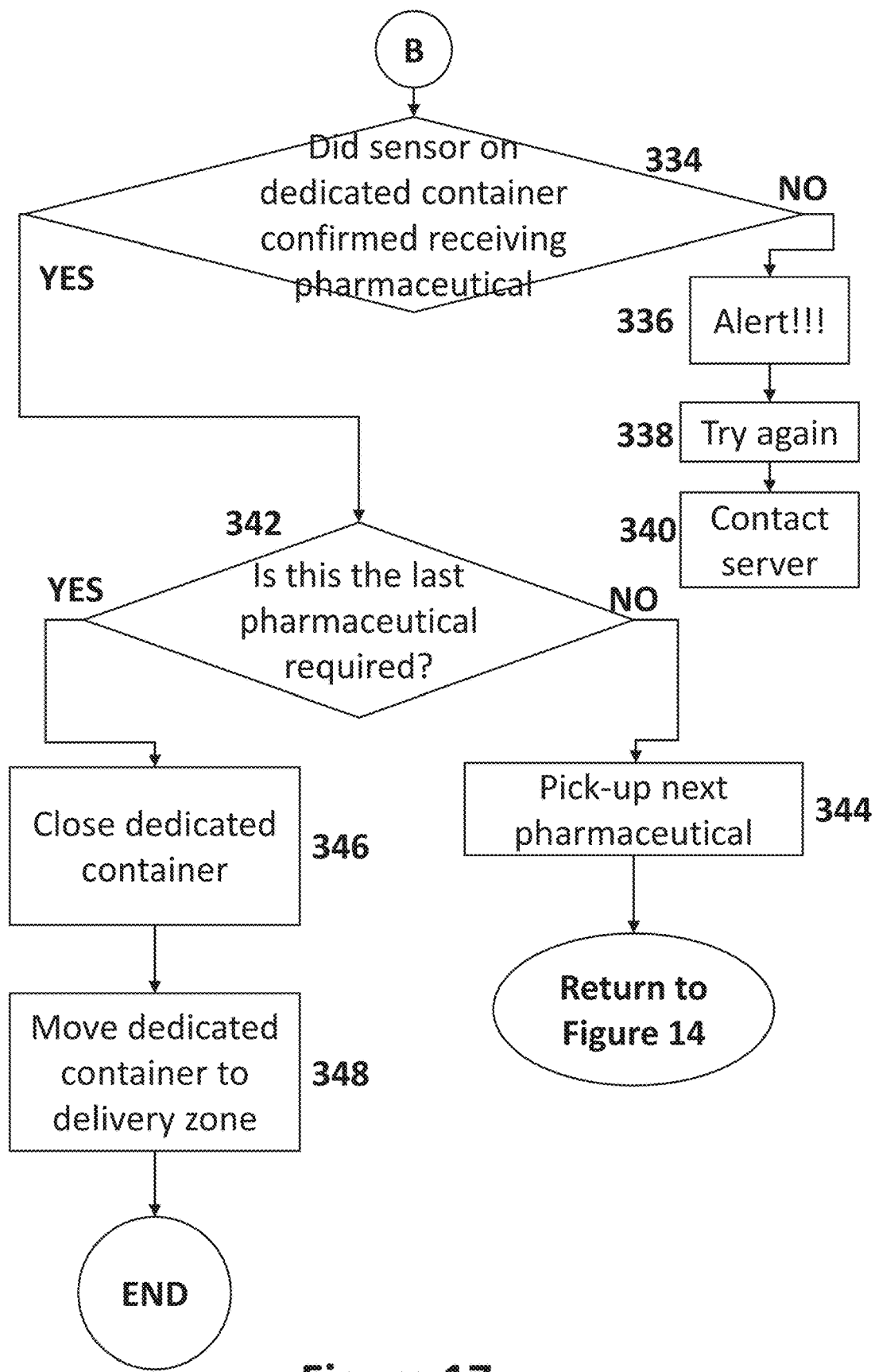
Figure 18:
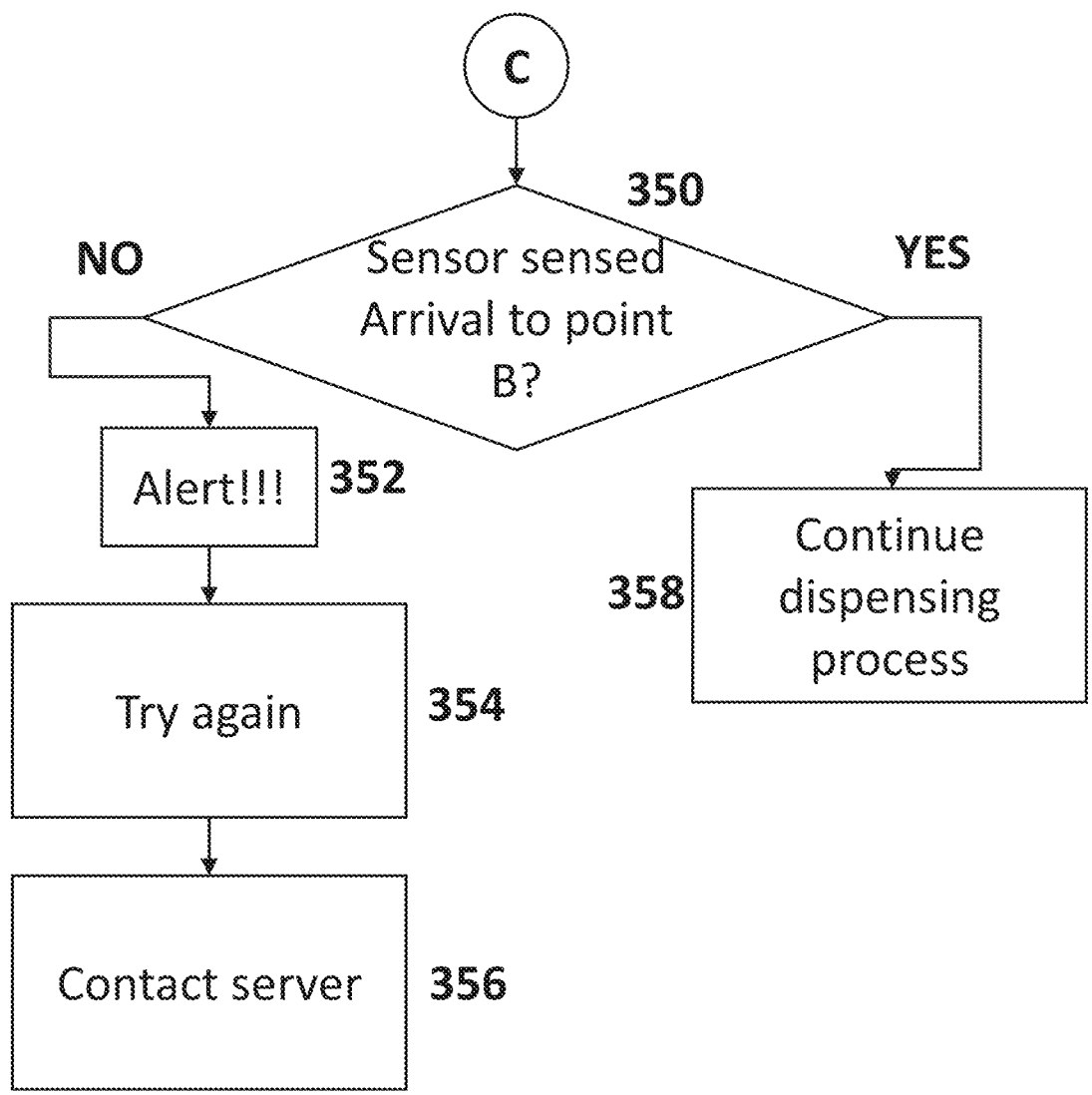

Referring now to FIG. 16, the continuation of a flow chart of an exemplary method, according to some embodiments of the invention. In some embodiments, the dedicated transportation element 108 arrives at the general container 102 and tries to pick up the pharmaceutical 316. In some embodiments, the system assesses if there is positive input from the sensor in the dedicated transportation element 108 that the pharmaceutical has been detected 318. In some embodiments, if the answer is "no" then the dedicated transportation element 108 will try to pick up again until the input is positive 320. In some embodiments, if the answer is "yes", then the dedicated transportation element 108 will transport the pharmaceutical from point A (in this example the general container 102) to point B 322 (in this example the dedicated container 106). In some embodiments, during the transportation the system will constantly assess the detection of the pharmaceutical in the dedicated transportation element 108 or the loss of detection thereof 324. In some embodiments, if the response is "yes" to the loss of detection, then the system sends an alert that a pharmaceutical has been lost 324 and returns to try to pick up again a pharmaceutical 320. In some embodiments, loss of a pharmaceutical can be double assessed with other sensors in the machine, for example video camera, sound sensor and/or vibration sensor. In some embodiments, during and/or while the in the dedicated transportation element 108 transports the pharmaceutical, the system confirms that the sensor located at the dedicated container has provided a positive input that the dedicated container is ready to receive pharmaceuticals 326. In some embodiments, if the answer is "no", meaning the dedicated container is not ready, then the system send an alert 328 and activates the control measures of the hardware that manipulates the dedicated container 330. In some embodiments, once all has been corrected, the sensor will send a confirmation that the dedicated container is ready to receive pharmaceuticals. In some embodiments, then the dedicated transportation element 108 will release the pharmaceutical into the dedicated container 332. The method continues following the letter B into FIG. 17. In some embodiments, in parallel, the system will assess if the sensor in the dedicated container has confirmed that the pharmaceutical has been delivered 334. In some embodiments, if the answer is "no", then the system sends an alert 336, commands the dedicated transportation element 108 to try again 338, and a message is sent to the server for monitoring reasons 340. In some embodiments, if the answer is "yes" then the system assesses if that was the last pharmaceutical needed to be inserted in the dedicated container 342. In some embodiments, if the answer is "no", then the dedicated transportation element 108 is sent to pick up the next pharmaceutical 344, which brings us back to FIG. 16. In some embodiments, if the answer is "yes" and that was the last pharmaceutical, the dedicated container is closed 346 monitored by the sensor dealing the dedicated container, and moved to a delivery zone in which ready to be dispensed dedicated containers wait to be dispensed 348. In some embodiments, closing the dedicated container includes also marking the dedicated container with information details of and/or for the specific user that needs to receive the pharmaceuticals.

Returning to FIG. 16, during the overall activity of the dedicated transportation element 108, sensors on the dedicated transportation element monitor the activity of the dedicated transportation element 108 itself. Following the letter C into FIG. 18, the system assesses if the sensor on the dedicated transportation element 108 has detected arrival to point B (or point A before that, or any movement of the dedicated transportation element) 350. In some embodiments, if the answer is "no", then the system send an alert 352 and commands the dedicated transportation element 108 to try again 354, in parallel a message is sent to the server for monitoring reasons 356. In some embodiments, as long the answer is "yes" the system continues with the dispensing process 358.

Exemplary Vacuum-Based Pharmaceutical Relaying Method

Figure 19:
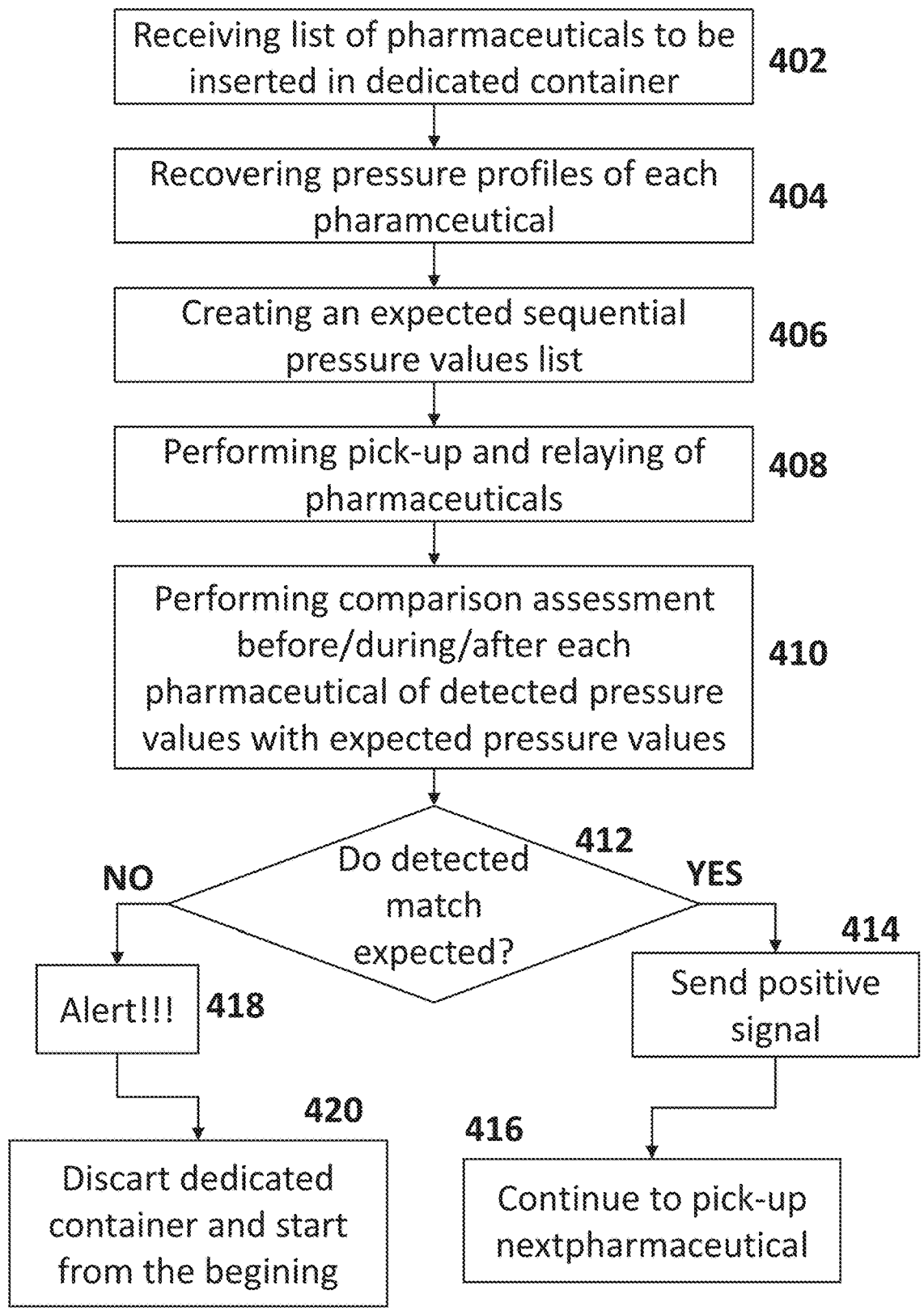

Referring now to FIG. 19, showing flowchart of an exemplary method when relaying a pharmaceutical using a vacuum-based elements, according to some embodiments of the invention. In some embodiments, the pharmaceutical dispensing machine receives a list of pharmaceuticals to be moved from generic containers to a dedicated container in order to be dispensed 402. In some embodiments, the pharmaceutical dispensing machine recovers from the server the pressure profiles of each of the pharmaceuticals that are need to be moved 404. In some embodiments, the pharmaceutical dispensing machine creates an expected sequential pressure value list 406 comprising all pharmaceuticals needed to be move and comprising the expected pressure values regarding the opening, holding and closing of the dedicated container. In some embodiments, the pharmaceutical dispensing machine performs the pick-up of each single individual pharmaceutical according to the list 408. In some embodiments, before/during/after each relaying of each pharmaceutical, the pharmaceutical dispensing machine performs a comparison assessment of the detected pressure values (from the sensors—as disclosed above) with the expected pressure values 410. In some embodiments, the pharmaceutical dispensing machine assesses if the detected pressure matches the expected pressure 412. In some embodiments, when the answer is "yes", then the pharmaceutical dispensing machine sends a positive signal to the server 414 and continues to pick up the next pharmaceutical 416. In some embodiments, if the answer is "no", then the pharmaceutical dispensing machine sends an alert to the server 418 and discards the dedicated container into the waste bin and commences the process from the beginning 420.

Exemplary Overall Monitoring Method

Figure 20:
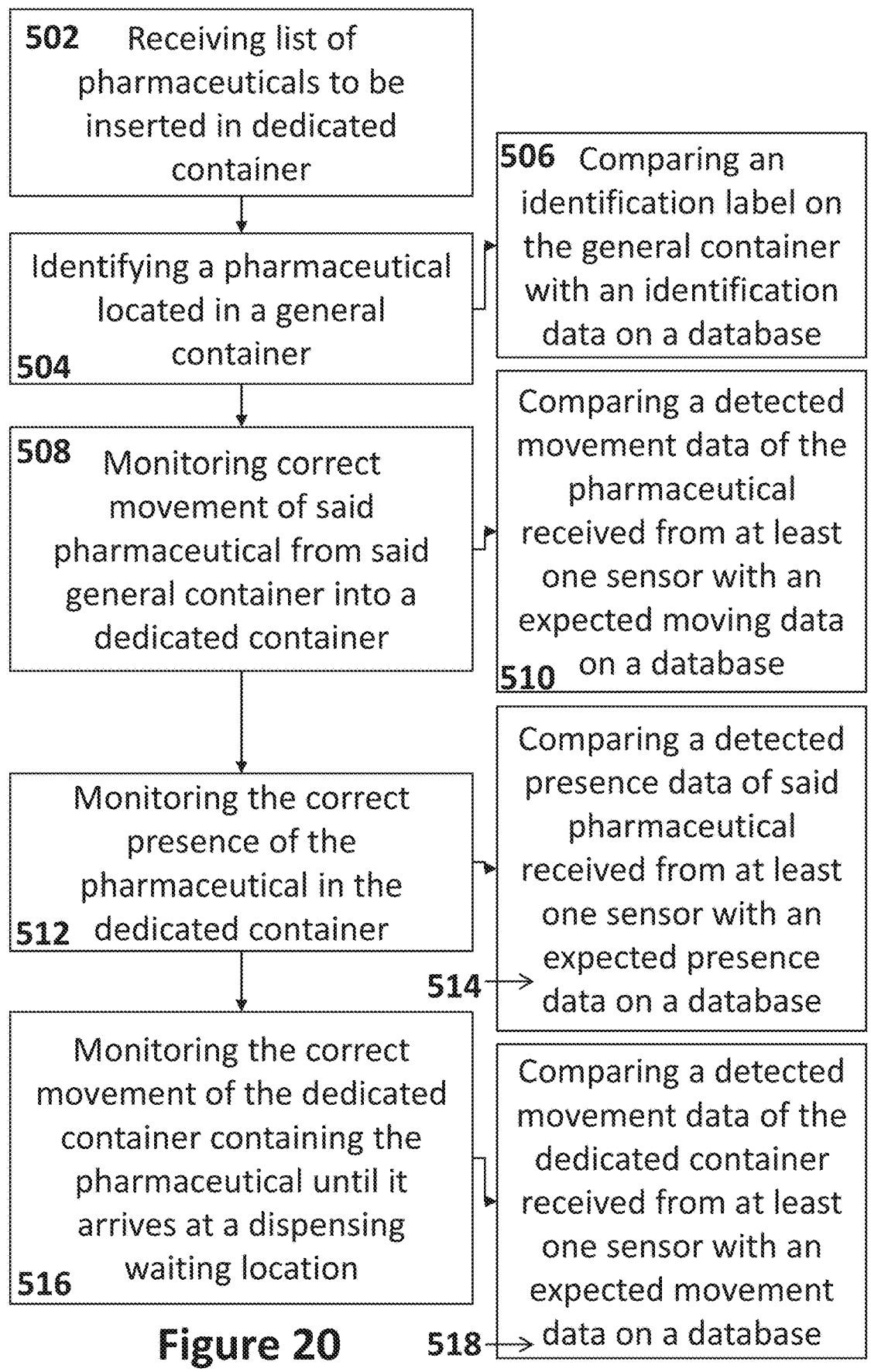

Referring now to FIG. 20, showing flowchart of an exemplary monitoring method of a pharmaceutical dispensing process performed by a pharmaceutical dispensing machine, according to some embodiments of the invention. In some embodiments, the pharmaceutical dispensing machine comprises a closed housing in which the pharmaceutical dispensing process is performed by a plurality of part within the closed housing, as disclosed herein elsewhere. In some embodiments, after receiving a list of pharmaceuticals to be inserted in a dedicated container 502, the pharmaceutical dispensing machine identifies the required pharmaceutical located in a general container 504. In some embodiments, the identification of the pharmaceutical located in said general container comprises comparing an identification label on the general container with an identification data on a database 506. In some embodiments, the pharmaceutical dispensing machine then monitors the correct movement of the pharmaceutical from the general container into a dedicated container 508. In some embodiments, the monitoring of the correct movement of the pharmaceutical from the general container into the dedicated container comprises comparing a detected movement data of the pharmaceutical received from at least one sensor with an expected moving data on a database 510. In some embodiments, the pharmaceutical dispensing machine then monitors the correct presence of the pharmaceutical in the dedicated container 512. In some embodiments, monitoring the correct presence of the pharmaceutical in the dedicated container comprises comparing a detected presence data of said pharmaceutical received from at least one sensor with an expected presence data on a database 514. In some embodiments, the pharmaceutical dispensing machine then monitors the correct movement of the dedicated container containing the pharmaceutical until it arrives at a dispensing waiting location 516. In some embodiments, monitoring the correct movement of the dedicated container containing the pharmaceutical until it arrives at a dispensing waiting location comprises comparing a detected movement data of the dedicated container received from at least one sensor with an expected movement data on a database 518. In some embodiments, a dispensing waiting location is a location within the pharmaceutical dispensing machine where ready-to-be-dispensed dedicated containers are moved and are waiting to be picked up from a user/dedicated personnel. In some embodiments, a dispensing waiting location is one or more of a tray, a box, an opening in the pharmaceutical dispensing machine accessible to the user/dedicated personnel. In some embodiments, the monitoring method of a pharmaceutical dispensing process comprises one or more of any of the abovementioned monitoring methods. In some embodiments, the monitoring method of a pharmaceutical dispensing process is an addition to one or more of any of the abovementioned monitoring methods.

Exemplary Response to Detection of Problems

In some embodiments, following an input received by the one or more sensors, the pharmaceutical dispensing machine performs one or more actions. In some embodiments, when the input received indicates an actual operational problem that causes the non-fulfillment of the pharmaceutical dispensing process, the pharmaceutical dispensing machine contacts the server requesting to activate alternative pharmaceutical dispensing sources capable to fulfill the pharmaceutical dispensing process, optionally to meet a pharmaceutical dispensing schedule. In some embodiments, alternative pharmaceutical dispensing sources can be other pharmaceutical dispensing devices and/or a pharmacy. Examples for alternative sources and activation of the alternative sources can be found in U.S. patent application Ser. No. 16/214,081, which is hereby incorporated herein by reference in its entirety. In some embodiments, when the input received indicates a potential operational problem that can possibly cause the non-fulfillment of the pharmaceutical dispensing process, the pharmaceutical dispensing machine contacts the server to dispatch a technician to check the pharmaceutical dispensing machine to potentially avoid a problem that will interfere with the fulfillment of the pharmaceutical dispensing schedule. In some embodiments, when the input received indicates that a pharmaceutical has been lost during the movement of the pharmaceutical from one location to the other, the pharmaceutical dispensing machine contacts the server to inform of this loss. In some embodiments, during the next visit of a technician, the technician will look for the missing pharmaceutical, and will check the potential source that caused the loss of the pharmaceutical to begin with.

Exemplary use of Waste Bin in a Pharmaceutical Dispensing Machine

In some embodiments, when either manipulation and/or filling of a dedicated container is recorded as failure, the dedicated container is immediately discarded, for example, into a waste bin. In some embodiments, dedicated containers are discarded when there is a doubt about them, for example when dedicated containers do not reach and/or are jammed when picked from the dedicated container's feeders; when dedicated containers are not picked properly from the feeder; when dedicated containers did not straighten; when dedicated containers do not open; when dedicated containers, while moving from one location to another, the vacuum sensor detected a non-expected pressure value; when dedicated containers, during the filling of pharmaceuticals, sensors picked a non-expected value; when dedicated containers after being close, sensor values show lower values than expected. In some embodiments, when a dedicated container is suspected to contain pharmaceuticals is discarded, a signal is generated to dedicated personnel notifying that a pharmaceutical might be located in the waste bin. In some embodiments, a potential advantage of this is to notify dedicated personnel when a sensitive pharmaceutical might be in the waste bin and allows recordation and recovery of the sensitive pharmaceuticals.

It is expected that during the life of a patent maturing from this application many relevant monitoring systems comprising one or more sensors will be developed; the scope of the term sensor is intended to include all such new technologies a priori.

As used herein with reference to quantity or value, the term "about" means "within ±20% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A pharmaceutical dispensing machine configured to perform a pharmaceutical dispensing process including recovering at least one pharmaceutical ready-to-be-taken-by-a-patient from a general container between a plurality of general containers, each general container containing different pharmaceuticals, and relaying said at least one pharmaceutical to the inside of at least one dedicated container, said pharmaceutical dispensing machine comprising:
   a plurality of parts where said at least one pharmaceutical is passed from one of said plurality of parts to another of said plurality of parts to perform said recovering and said relaying;
   a controller comprising a memory storing indication of information regarding said pharmaceutical dispensing process;
   a plurality of sensors;
   wherein said controller utilizes at least one sensor from said plurality of sensors to detect a deviation from expected predetermined detection values related to said recovering and said relaying of said at least one pharmaceutical; same said at least one sensor being used for detecting said deviation for all of said plurality of general containers;
   wherein said plurality of parts comprise a transportation element configured to perform said relaying by transporting said at least one pharmaceutical from said general container into the inside of said at least one dedicated container while said general container does not move;
   wherein said at least one sensor is configured to move together with said transportation element and further configured to detect if said at least one pharmaceutical has been lost during said recovering and said relaying.

2. The pharmaceutical dispensing machine according to claim 1, further comprising a pharmaceutical identification element configured to identify said at least one pharmaceutical before said at least one pharmaceutical is passed from one part to another part.

3. The pharmaceutical dispensing machine according to claim 1, wherein the cause that said at least one pharmaceutical is not detected according to expected predetermined detection values is that said at least one pharmaceutical fell.

4. The pharmaceutical dispensing machine according to claim 1, wherein said one or more sensors are further configured to monitor the hardware that actuates said pharmaceutical dispensing process.

5. The pharmaceutical dispensing machine according to claim 1, wherein said one or more sensors are one or more of weight sensors configured to detect said at least one pharmaceutical when in said at least one dedicated container.

6. The pharmaceutical dispensing machine according to claim 1, wherein said one or more sensors are one or more of optical sensors configured to monitor one or more of movement of said at least one pharmaceutical and status of said at least one dedicated container.

7. The pharmaceutical dispensing machine according to claim 1, wherein said one or more sensors are one or more of vibration sensors configured to monitor vibrations of one or more of said pharmaceutical dispensing machine in general, said plurality of parts and a bottom of said pharmaceutical dispensing machine.

8. The pharmaceutical dispensing machine according to claim 1, wherein said one or more sensors are one or more of sound sensors configured to monitor sounds emitted from one or more of said pharmaceutical dispensing machine in general, said plurality of parts, sounds detected at a bottom of said pharmaceutical dispensing machine and sounds detected outside said pharmaceutical dispensing machine.

9. The pharmaceutical dispensing machine according to claim 1, wherein said one or more sensors are one or more of vacuum sensors configured to monitor vacuum values of one or more of a part of said pharmaceutical dispensing machine that performs said relaying of said at least one pharmaceutical, a part of said pharmaceutical dispensing machine that performs opening of said at least one dedicated container, a part of said pharmaceutical dispensing machine that picks up said at least one dedicated container and a part of said pharmaceutical dispensing machine that provides vacuum to said one or more parts.

10. The pharmaceutical dispensing machine according to claim 9, wherein said plurality of parts comprise at least one vacuum-based relaying part comprising said one or more of vacuum sensors.

11. The pharmaceutical dispensing machine according to claim 1, wherein said pharmaceutical dispensing machine further comprises a video camera configured to visually monitor said pharmaceutical dispensing process.

12. The pharmaceutical dispensing machine according to claim 1, wherein said one or more sensors are configured to provide detection data and said pharmaceutical dispensing machine is configured to compare said detection data with a database of known detection data in order to identify said detection data.

13. The pharmaceutical dispensing machine according to claim 8, wherein said one or more sound sensors are configured to detect the noise made due to said at least one pharmaceutical falling inside said pharmaceutical dispensing machine.

14. The pharmaceutical dispensing machine according to claim 7, wherein said one or more vibration sensors are configured to detect the vibration made due to said at least one pharmaceutical falling inside said pharmaceutical dispensing machine.

15. The pharmaceutical dispensing machine according to claim 1, wherein said one or more sensors are configured to alert when said dedicated containers contain a different number of pills than expected.

16. The pharmaceutical dispensing machine according to claim 1, wherein said one or more sensors are configured to alert when said dedicated containers contain a different type of pharmaceutical than expected.

17. The pharmaceutical dispensing machine according to claim 1, wherein said information regarding said pharmaceutical dispensing process includes an order in which said at least one pharmaceutical is recovered and relayed from said general container to said at least one dedicated container.

18. The pharmaceutical dispensing machine according to claim 1, wherein at least one sensor from said plurality of sensors moves together with said at least one pharmaceutical after said recovering and said relaying.

19. The pharmaceutical dispensing machine according to claim 1, wherein said recovering is performed by picking up said at least one pharmaceutical.

20. The pharmaceutical dispensing machine according to claim 19, wherein said plurality of parts are configured to perform said picking up.

21. The pharmaceutical dispensing machine according to claim 19, wherein said information regarding said pharmaceutical dispensing process comprises information regarding said picking up of said at least one pharmaceutical.

22. The pharmaceutical dispensing machine according to claim 19, wherein said controller further utilizes said plurality of sensors to detect a deviation from expected predetermined detection values related to said picking up.

23. The pharmaceutical dispensing machine according to claim 19, wherein said plurality of parts comprise a picker to perform said picking up.

24. The pharmaceutical dispensing machine according to claim 23, wherein said picker comprises at least one sensor.

25. The pharmaceutical dispensing machine according to claim 24, wherein said controller further utilizes said sensor in said picker to detect a deviation from expected predetermined detection values related to said picking up.

* * * * *